(12) United States Patent
Khine et al.

(10) Patent No.: US 11,207,002 B2
(45) Date of Patent: *Dec. 28, 2021

(54) FETAL HEALTH MONITOR

(71) Applicant: The Regents of the University of California, Oakland, CA (US)

(72) Inventors: Michelle Khine, Irvine, CA (US); Jonathan Pegan, Irvine, CA (US); Eugene Lee, Irvine, CA (US); Mark Bachman, Irvine, CA (US); Joshua Kim, Oakland, CA (US); Sun-Jun Park, Oakland, CA (US); Gareth Forde, Irvine, CA (US); Dorsey Ligon, Grand Rapids, MI (US)

(*) Notice: Subject to any disclaimer, the term of this patent is extended or adjusted under 35 U.S.C. 154(b) by 201 days.

This patent is subject to a terminal disclaimer.

(21) Appl. No.: 15/312,030

(22) PCT Filed: May 18, 2015

(86) PCT No.: PCT/US2015/031442
§ 371 (c)(1),
(2) Date: Nov. 17, 2016

(87) PCT Pub. No.: WO2015/179322
PCT Pub. Date: Nov. 26, 2015

(65) Prior Publication Data
US 2017/0086709 A1 Mar. 30, 2017

Related U.S. Application Data

(60) Provisional application No. 62/000,463, filed on May 19, 2014, provisional application No. 62/088,486, (Continued)

(51) Int. Cl.
*A61B 5/11* (2006.01)
*A61B 5/00* (2006.01)
(Continued)

(52) U.S. Cl.
CPC ............. *A61B 5/11* (2013.01); *A61B 5/6833* (2013.01); *G16H 40/67* (2018.01); *G16H 50/20* (2018.01);
(Continued)

(58) Field of Classification Search
CPC ....... G06F 3/044; G06F 3/0414; G07C 5/008; G07C 5/0808; H01L 2924/0002; A61B 5/11; G16H 50/20
See application file for complete search history.

(56) References Cited

U.S. PATENT DOCUMENTS 5,079,535 A * 1/1992 Neuman ............... A61B 5/1135
338/2
2002/0130673 A1 9/2002 Pelrine et al.
(Continued)

FOREIGN PATENT DOCUMENTS

| CN | 103219066 A | 7/2013 |
|---|---|---|
| WO | WO 2014/066802 A1 | 5/2014 |
| WO | WO 2015/179320 A1 | 11/2015 |

OTHER PUBLICATIONS

Khang et al. 'Molecular Scale Buckling Mechanics in Individual Aligned Single-Wall Carbon Nanotubes on Elastomeric Substrates'; Nano Letters 2008 vol. 8, No. 1 pp. 124-130 (Year: 2008).*

(Continued)

*Primary Examiner* — Patrick Fernandes
(74) *Attorney, Agent, or Firm* — Knobbe, Martens, Olson & Bear, LLP

(57) ABSTRACT

A wearable sensor apparatus is disclosed that includes a flexible substrate adapted to be coupled with a skin surface of an expectant mother. A conductor is disposed on the flexible substrate. The conductor can include micron-scale invaginations. The conductor can be capable of repeatable variation in resistance when subject to a strain. Also disclosed is a system for monitoring the health of a fetus in
(Continued)

utero that includes a wearable sensor apparatus. The wearable sensor apparatus is configured to output a signal responsive to an electrical input. The system includes a computing system with one or more hardware processors. The computing system is programmed to implement a signal processing module configured to access the output signal from the wearable strain gauge and generate an output indicative of health of the baby in utero. The output can be based in part on the received output signal and previously stored correlations between signal data from the wearable strain gauge and observations of the system or of the mother. A user interface module can be provided and can be configured to display an output indicative of health of the baby in utero.

26 Claims, 22 Drawing Sheets

Related U.S. Application Data filed on Dec. 5, 2014, provisional application No. 62/147,979, filed on Apr. 15, 2015.

(51) Int. Cl.
*G16H 40/67* (2018.01)
*G16H 50/20* (2018.01)

(52) U.S. Cl.
CPC ... *A61B 2503/02* (2013.01); *A61B 2562/0261* (2013.01)

(56) References Cited

U.S. PATENT DOCUMENTS

| | | | |
|---|---|---|---|
| 2005/0080349 | A1 | 4/2005 | Okada et al. |
| 2006/0169989 | A1 | 8/2006 | Bhattacharya et al. |
| 2006/0283262 | A1 | 12/2006 | Smits et al. |
| 2008/0119896 | A1 | 5/2008 | Wong et al. |
| 2011/0137577 | A1* | 6/2011 | Chen ............... B82Y 15/00 702/42 |
| 2011/0253288 | A1 | 10/2011 | Xie |
| 2011/0278040 | A1 | 11/2011 | Zhang et al. |
| 2012/0035508 | A1 | 2/2012 | Van Leer |
| 2012/0086433 | A1 | 4/2012 | Cheng et al. |
| 2012/0121870 | A1 | 5/2012 | Toury et al. |
| 2013/0140611 | A1 | 6/2013 | Kim et al. |
| 2013/0264912 | A1 | 10/2013 | Kwon et al. |
| 2013/0281861 | A1 | 10/2013 | Flomerfelt et al. |
| 2013/0312541 | A1 | 11/2013 | Majidi et al. |
| 2014/0054599 | A1 | 2/2014 | Choi et al. |
| 2014/0290376 | A1* | 10/2014 | Rahajandraibe ......... G01L 1/22 73/763 |
| 2015/0034237 | A1 | 2/2015 | Biggs et al. |
| 2015/0263235 | A1 | 9/2015 | Shin et al. |
| 2015/0294805 | A1 | 10/2015 | Hayward et al. |

OTHER PUBLICATIONS

Herrmann et al. 'Nanoparticle films as sensitive strain gauges'; Appl. Phys. Lett. 91, 183105 (2007) ttps://doi.org/10.1063/1.2805026 (Year: 2007).*

Tanner et al. 'Nanoparticle strain sensor' Proc. Eurosensors XXV, Sep. 4-7, 2011 (Year: 2011).*

Sangeetha et al. 'Nanoparticle-Based Strain Gauges Fabricated by Convective Self Assembly: Strain Sensitivity and Hysteresis with Respect to Nanoparticle Sizes'; J. Phys. Chem. C 2013, 117, 1935-1940 (Year: 2012).*

Ma et al. 'Micro-strain sensing using wrinkled stiff thin films on soft substrates as tunable optical grating' May 20, 2013 | vol. 21, No. 10 | DOI:10.1364/OE.21.011994 | Optics Express 11994 (Year: 2013).*

Pegan, et al. 2013 "Flexible shrink-induced high surface area electrodes for electrochemiluminescent sensing." *Lab Chip* 13: 4205-4209.

Ausman et al. 2000 "Organic Solvent Dispersions of Single-Walled Carbon Nanotubes: Toward Solutions of Pristine Nanotubes" *J Phys Chem B* 104: 8911-8915.

Bandodkar, A.J., and Wang, J. 2014. "Non-invasive wearable electrochemical sensors: a review" *Trends Biotechnol* 32: 363-371.

Biagiotti, V. et al. 2012 "Probe accessibility effects on the performance of electrochemical biosensors employing DNA monolayers" *Anal. Bioanal. Chem.* 402: 413-421.

Byun I. et al. 2013 "Transfer of thin Au films to polydimethylsiloxane (PDMS) with reliable bonding using (3-mercaptopropyl)trimethoxysilane (MPTMS) as a molecular adhesive" *J Micromech Microeng* 23(8): 1-10.

Chen et al. 1997 "Estimation of central aortic pressure waveform by mathematical transformation of radial tonometry pressure" *Circulation* 95:1827-1836.

Chirinos, J. A. et al. 2011 "Ethnic differences in arterial wave reflections and normative equations for augmentation index" *Hypertension* 57: 1108-1116.

Drelich, J. and Chibowski, E. 2010 "Superhydrophilic and superwetting surfaces: Definition and mechanisms of control" *Langmuir* 26: 18621-18623.

Dumonteil et al. 2006 "Dispersion of carbon nanotubes using organic solvents" J Nanosci Nanotechnol 6(5): 1315-1318.

Freschauf, L.R. et al. 2012 "Shrink-induced superhydrophobic and antibacterial surfaces in consumer plastics" *PLoS One* 7: e40987 (in 7 pages).

Fu et al. 2009 "Tunable nanowrinkles on shape memory polymer sheets" *Adv Mater* 21: 4472-4476.

Gabardo, C. et al. 2013 "Bench-top fabrication of hierarchically structured high surface-area electrodes" *Adv. Funct. Mater.* 23: 3030-3039.

Gabardo, C.M. et al. 2015 "Rapid prototyping of microfluidic devices with integrated wrinkled gold micro-/nano textured electrodes for electrochemical analysis" *Analyst* 140: 5781-5788.

Hauke et al. 2017 "Superwetting and aptamer functionalized shrink-induced high surface area electrochemical sensors" *Biosensors and Bioelectronics* 94: 438-442.

Heikenfeld, J., 2016 "Non-invasive analyte access and sensing through eccrine sweat: challenges and outlook circa 2016" *Electroanalysis* 28: 1242-1249.

Kimmel, D.W. et al. 2012 "Electrochemical sensors and biosensors" *Anal. Chem.* 84: 685-707.

Kohara, K. et al. 2005 "Radial augmentation index: A useful and easily obtainable parameter for vascular aging" *Am J Hypertens* 18: 14-17.

Li et al. 2012 "Dispersion of Carbon Nanotubes in Organic Solvents Initiated by Hydrogen Bonding Interactions" *AIChE Journal* 58: 2997-3002.

Lipomi et al. 2011 "Skin-like pressure and strain sensors based on transparent elastic films of carbon nanotubes" *Nature Nanotechnology* 6: 788-792.

Lubin, A.A. and Plaxco, K.P., 2010 "Folding-based electrochemical biosensors: the case for responsive nucleic acid architectures" *Acc. Chem. Res.* 43: 496-505.

Nelson et al., 2010 "Noninvasive Measurement of Central Vascular Pressures With Arterial Tonometry: Clinical Revival of the Pulse Pressure Waveform?" *Mayo Clin Proc* 85(5): 460-472.

Pheeny, C.G. and Barton, J.K. 2012 "DNA electrochemistry with tethered methylene blue" *Langmuir* 28: 7063-7070.

Rowe, A.A. et al. 2010 "Reagentless measurement of aminoglycoside antibiotics in blood serum via an electrochemical, ribonucleic acid aptamer-based biosensor" *Anal. Chem.* 82: 7090-7095.

Salvarezza, R.C. et al. 1990 "Monte Carlo simulation applicable to the growth of rough metal overlayers: parametric relationships related to the electrochemical roughening" *Phys. Rev. B* 41: 502-512.

Schwartz et al. (2013 "Flexible polymer transistors with high pressure sensitivity for application in electronic skin and health monitoring" *Nature Communications* 4: 1859 (in 8 pages).

(56) References Cited

OTHER PUBLICATIONS

Setia, U. and Gross, P.A. 1976 "Administration of tobramycin and gentamicin by the intravenous route every 6 h in patients with normal renal function" *J. Infect. Dis*. 134: S125-129.

Sonney, S. et al. 2015 "Rapid bench-top fabrication of poly(dimethylsiloxane), polystyrene microfluidic devices incorporating high-surface area sensing electrodes" *Biomicrofluidics* 9: 026501 (in 11 pages).

Wang et al. 2014 "Silk-Molded Flexible, Ultrasensitive, and Highly Stable Electronic Skin for Monitoring Human Physiological Signals" *Advanced Materials* 26: 1336-1342.

* cited by examiner

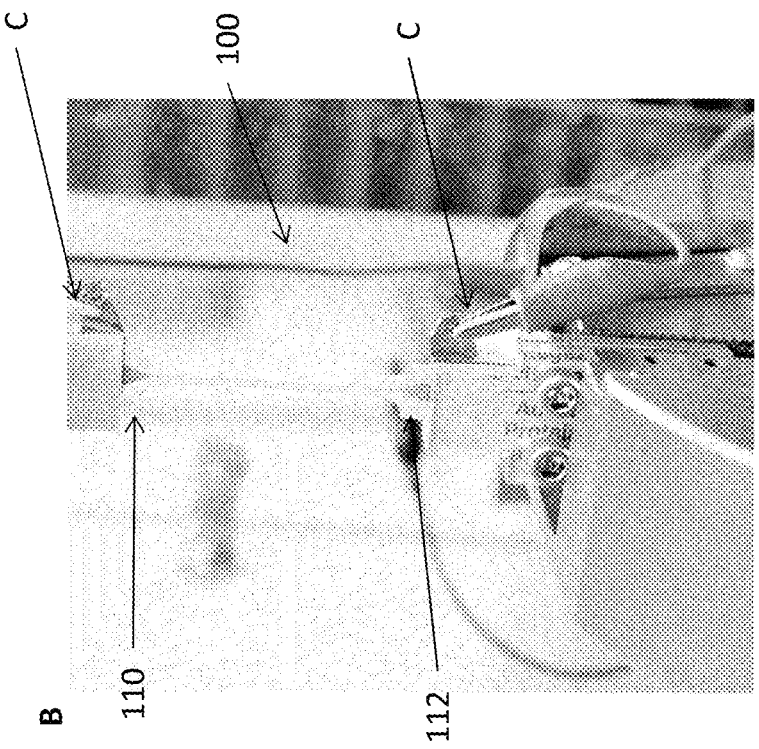
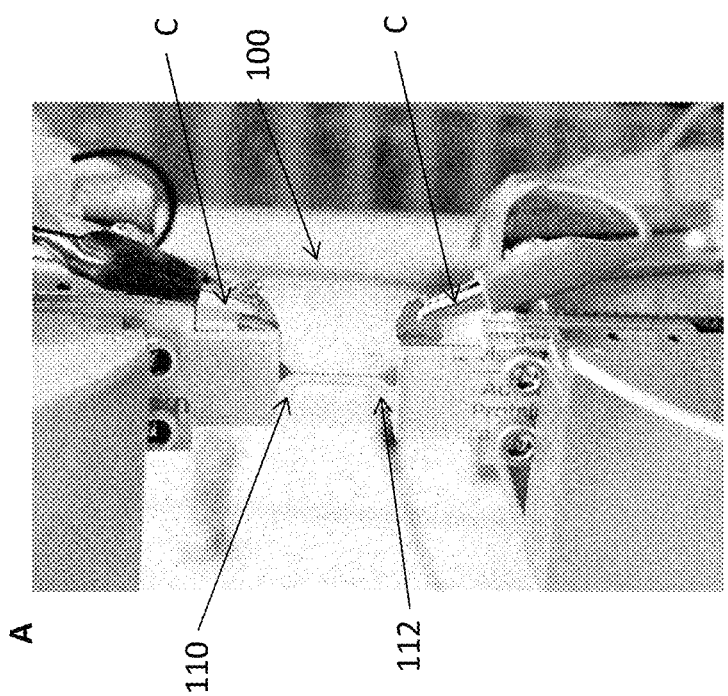
Fig. 8

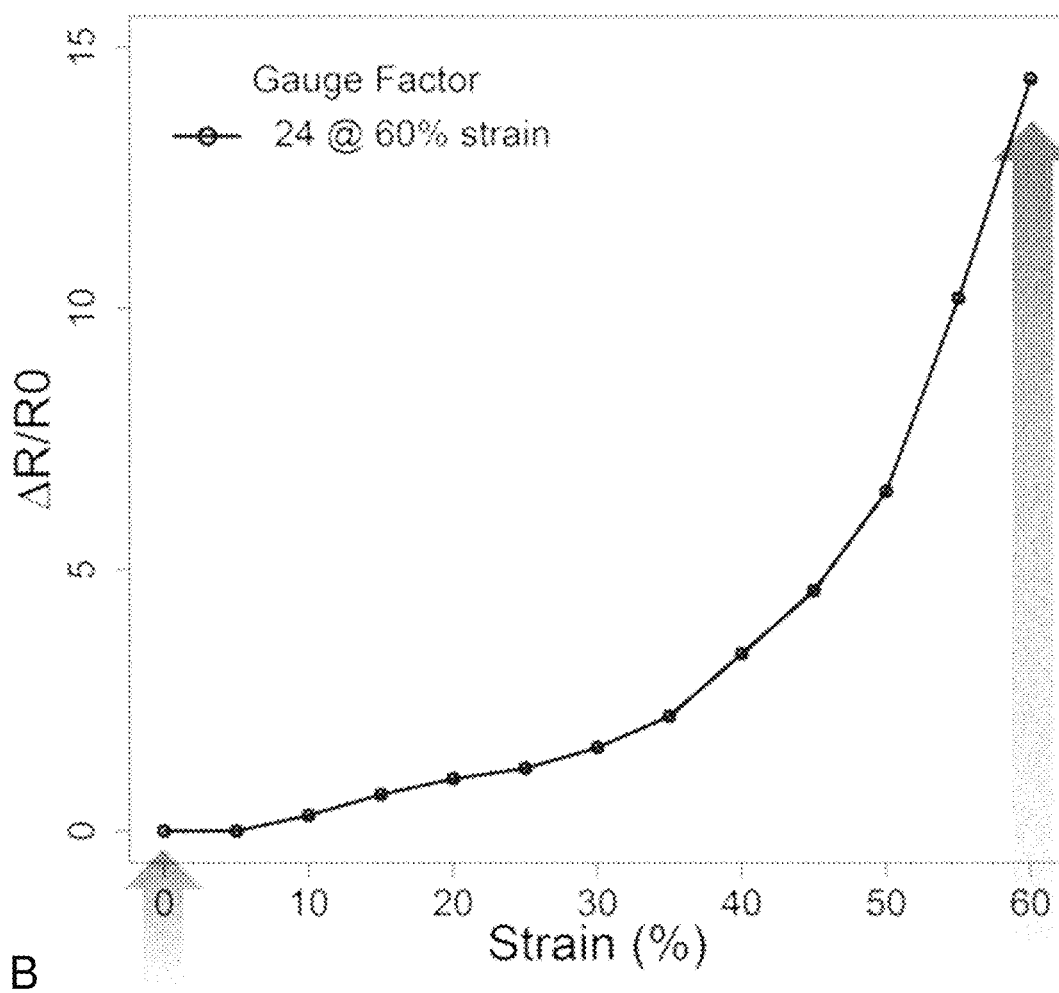
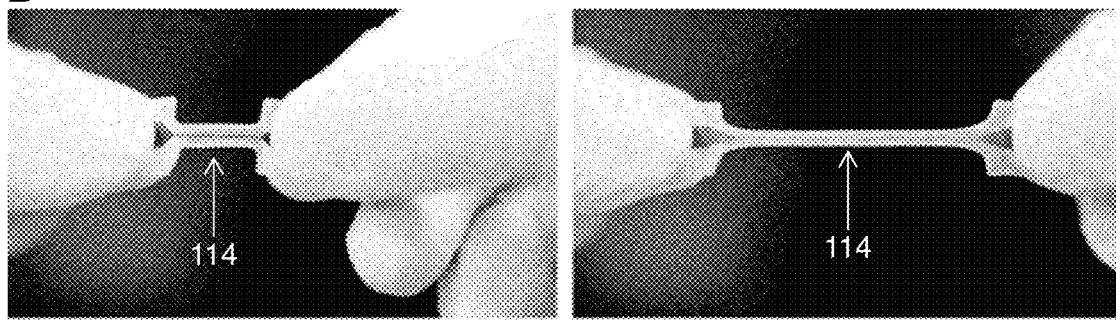
Fig. 11

Before Shrinking
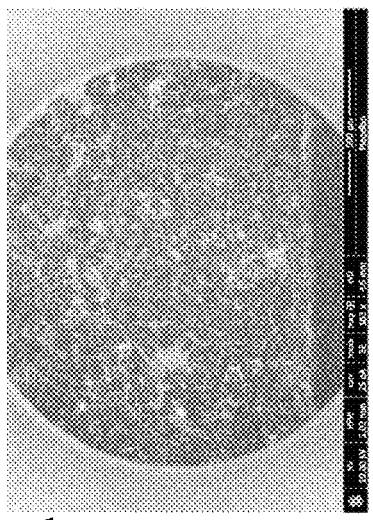
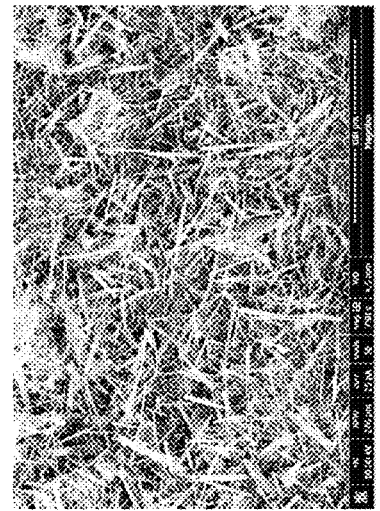
After Shrinking
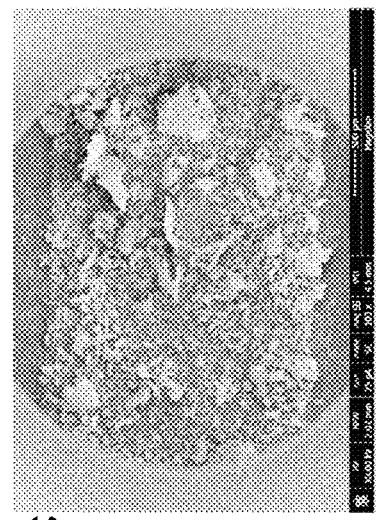
Fig. 15

FETAL HEALTH MONITOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This application is directed to systems, methods and apparatuses for monitoring the health of a baby in utero.

Description of the Related Art

There are currently approximately 4 million pregnant women in the United States. Although extensive complex diagnostic technology is available in sophisticated clinical settings, there are no marketed products for continuously monitoring the health of a baby in-utero.

The current standard of care for monitoring and predicting pregnancy outcome is primitive. In one prevalent method, the mother is instructed to count the number of times the baby kicks. The American Congress of Obstetricians and Gynecologists (ACOG) recommends that the mother keep track of how long it takes for her to feel 10 "kicks, flutters, swishes, or rolls". The mother is asked to track this at least twice per day and to record this information in a notebook. If the mother does not perceive at least 10 kicks within 2 hours, she is to contact her health care provider immediately.

This subjective approach is inaccurate. It can lead to false alarms, resulting in dangerous maternal stress and an increased burden on the health care system. Perhaps even worse, it can also lead to false negatives, where despite an emergency condition the mother fails to notice lessening or no movement of her baby. This inattention to decline in the baby's heath can result in a lack of proper medical intervention during the critical time frame when the baby could be saved.

Existing technologies, such as fetal heart rate monitor systems, fall short in addressing the need to non-invasively, continuously, and un-obtrusively monitor the health of the baby on a daily basis without tethers or interference with the mother's daily activities.

SUMMARY OF THE INVENTION

The present disclosure relates generally to a wearable sensor for monitoring fetal movement (e.g., fetal kicks) and/or health. The disclosure relates to technology for monitoring fetal health during later stages (e.g., weeks 24+) of pregnancy. More specifically, a sensor can be worn by a mother to extract biometric data about the fetus. This data can be used as an indirect indicator of fetal health.

We disclose wearable strain sensors that can detect fetal movement by externally measuring the activity of the fetus, quantified by the frequency of movement. Such a sensor can be worn at all times by the mother to continuously provide quantitative information. This wearable sensor is less cumbersome then existing technology to improve user compliance. With continuous monitoring a decline in fetal movement can be detected earlier then without this device.

Some embodiments relate to a method of monitoring fetal health in utero, comprising coupling a sensor apparatus to an abdominal surface of a patient, the sensor apparatus including a crumpled conductor capable of detecting strain. Current through the sensor apparatus can be detected during flexing of the surface. A characteristic of the sensor apparatus can be measured based on the strain to generate an output for a user indicative of the fetal health.

Some embodiments relate to a sensor apparatus comprising:

a flexible substrate adapted to be coupled with a portion of (e.g., the belly or abdomen of) a pregnant mother, and a conductor disposed on or in the flexible substrate, wherein the conductor is capable of repeatable variation in resistance when subject to a strain induced by motion of a fetus, e.g., strain of up to about 900%.

In some embodiments, the conductor is capable of a repeatable detection of variation in resistance when subject to a strain of up to about 330%.

In some embodiments, the conductor is capable of a repeatable detection of variation in resistance when subject to a strain of up to about 300%.

In some embodiments, the conductor is capable of a repeatable detection of variation in resistance when subject to a strain of up to about 150%.

In some embodiments, the metal film conductor is capable of a repeatable detection of variation in resistance when subject to a strain of more than 5%, 10%, 15%, 20%, 30%, 40%, 50%, 60%, 70%, 80%, 90%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, up to about 900%.

In some embodiments, the conductor comprises secondary folding.

In some embodiments, the secondary folding comprises micron-scaled invaginations in the surface of the conductor.

In some embodiments, the conductor comprises a metal film

In some embodiments, the conductor comprises any material suitable for processes conventionally used for semiconductor fabrication, e.g., sputtering or deposition, or comprise a material or configuration selected from the group consisting of a semiconductor structure, carbon nanotubes, nanowires and other one-dimensional structure, and carbon black.

In some embodiments, the metal film comprises a gold layer.

In some embodiments, the metal film comprises a platinum layer.

In some embodiments, the flexible substrate comprises an elastomeric polymer.

In some embodiments, the elastomeric polymer is an elastomeric silicone film.

In some embodiments, the elastomeric silicone film comprises polydimethylsiloxane.

In some embodiments, the elastomeric polymer is ECOFLEX™ from Smooth-on, Inc., which uses a platinum curing agent. ECOFLEX™ is softer than PDMS, and correspondingly more stretchable.

Some embodiments relate to a strain gauge, comprising:

a flexible substrate adapted to be coupled with a skin surface of a pregnant person, and a conductor deposited on the flexible substrate, wherein the conductor comprises micron-scale invaginations, wherein the strain gauge is adapted to provide a changing signal responsive fetal motion.

In some embodiments, the micron-scale invaginations comprise a heterogeneous structure.

In some embodiments, the flexible substrate is configured to be mounted to the skin of a user or patient.

Some embodiments relate to a method of making a sensor apparatus, comprising:

placing a polymeric sheet between a support and a mask configured to block regions of the polymeric sheet, depositing a conductive structure on the polymeric sheet at regions exposed through the mask, shrinking the polymeric sheet with conductive structure patterned on its surface by heating, optionally adding an adhesive layer to the conductive structure, and transferring the conductive structure to a flexible substrate, wherein the conductive structure when coupled with the flexible substrate and when coupled with a pregnant person is adapted to sense movements of a fetus within the pregnant person.

In some methods, the flexible substrate is an elastomeric polymer.

In some embodiments, the method further comprising casting the flexible substrate on the same surface of the polymeric sheet where the conductive structure is deposited.

In some methods, the polymeric sheet comprises a shape-memory shrink-wrap) two dimensional structure such as a polyolefin (PO) or other polymeric film.

In some methods, the polymeric sheet comprises polystyrene.

Some embodiments relate to a method of sensing a fetal health status, comprising:

coupling a sensor apparatus to a surface of a mother overlying a fetus, the sensor apparatus including a crumpled conductor capable of detecting strain;

directing current through the sensor apparatus during flexing of the surface; and measuring a characteristic of the sensor apparatus based on the strain to generate an output for a user indicative of the fetal health status.

In some embodiments, the characteristic of the sensor is a change in the resistance of a conductor thereof.

In some embodiments, movement of the surface is in response to breathing of the patient or user and the output indicates respiration of the user or patient.

In some embodiments, movement of the surface is in response to motion of the underlying structure.

Also disclosed is a process to densify and align one dimension nanostructuress, such as carbon nanotubes (CNTs) or silicon nanowires (SiNWs), comprising depositing a thin film of a one dimension nanostructures, such as CNTs or SiNWs on the surface of a shape memory polymer and shrinking the thin film of CNTs or SiNWs in at least one direction.

In some embodiments, the process further comprises uniaxially shrinking the thin film.

In some embodiments, the process further comprises biaxially shrinking the thin film.

In some embodiments, the shape memory polymer is a chemically resistant shape memory polymer.

In some embodiments, the shape memory polymer is a polyolefin.

In some embodiments, the CNTs or the Si NWs deposited on the surface of the shape memory polymer is dispersed in a solution of an organic solvent.

In some embodiments, the organic solvent is chloroform.

In some embodiments, the shape memory polymer is placed on the surface of an aqueous solution during said depositing a thin film of CNTs or SiNWs on the surface of a shape memory polymer.

In some embodiments, the uniaxially, biaxially, or multiaxially shrinking the thin film of CNTs or the thin film of SiNWs can be done by heating.

In some embodiments, the heating is done at a temperature of from 50-250° C.

In some embodiments, the heating is done at a temperature of 150° C.

In some embodiments, the thin film of CNTs or the thin film of SiNWs is deposited on the surface of the shape memory polymer with an airbrush.

Some embodiments relate to a film of highly dense and aligned carbon nanotubes prepared by the disclosed processes of densifying and aligning carbon nanotubes (CNTs) or silicon nanowires (SiNWs) comprising depositing a thin film of CNTs or a thin film of SiNWs on the surface of a shape memory polymer and shrinking the thin film of CNTs or the thin film of SiNWs in at least one direction.

In some embodiments of film, the density of CNTs or SiNWs results in a light transmittance value of about 40%.

In some embodiments of film, the electrical resistance of the film is about 300 kΩ.

Some embodiments relate to a method, comprising: forming a film of carbon nanotubes (CNTs) or silicon nanowires (SiNWs) on a substrate, the nanotubes having an average separation in a direction transverse to longitudinal axes thereof; and reducing the average separation of the nanotubes by shrinking the substrate in one direction.

Some embodiments relate to a method of forming a wrinkled CNT film or a wrinkled SiNW film, comprising: forming a film of carbon nanotubes (CNTs) or a thin film of silicon nanowires SiNWs on a substrate; and reducing the average separation of the nanotubes by biaxially or multiaxially shrinking the substrate, thereby forming the wrinkled CNT film or the wrinkled SiNW film.

Some embodiments relate to a system for monitoring the health of a fetus in utero. The system can include a wearable sensor apparatus. The wearable sensor apparatus can be configured to output a signal responsive to an electrical input. The system for monitoring health can include a computing system with one or more hardware processors. The computing system can be programmed to implement a signal processing module configured to access the output signal from a wearable strain gauge. The computing system can generate an output indicative of health of the baby in utero. The output can be based in part on the received output signal. The output can be based in part on previously stored correlations between signal data from a wearable strain gauge and observations of the system or of the mother. The computing system can include a user interface module configured to display the output indicative of health of the baby in utero.

In another embodiment, a wearable device is provided that comprises a stretchable interconnect for coupled with one or more electrical components. For example, in one embodiment, a first electrical component and a second electrical component are provided. The stretchable interconnect is disposed between the first electrical component and the second electrical component. The stretchable interconnect has a strain relieving configuration that provides a first regime of elongation in which no strain is applied to a conductor disposed in the interconnect. The stretchable interconnect has a second regime of elongation in which measurable strain is applied to the conductor. The stretchable interconnect can allow an electrical path to be subject to a range of movement. The stretchable interconnect can allow an electrical path to be provided about non-planar boundaries between the first electrical component and the second electrical component without affecting the electrical signal through the conductor. A stretchable interconnect provides mechanical isolation between a component that is sensitive to external mechanical loads, such as a strain sensor.

BRIEF DESCRIPTION OF THE DRAWINGS

FIG. 8 (A and B) show mechanical integrity tests for an embodiment of a sensor apparatus.

FIG. 10 (B). Changes in resistance (ΔR/Ro) are measured as a function of elbow flexing.

FIG. 11 (A) changes in resistance (ΔR/Ro) as a function of linear sensor stretch for sensor apparatus. FIG. 11 (B) includes photographs of a sensor before and after linear stretch to 60% strain.

FIG. 15 shows SEM images of silicon nanowire films before and after shrinking. (A) Before shrinking, 102× magnification; (B) before shrinking, 750× magnification; (C) after shrinking, 103× magnification; (D) after shrinking, 750× magnification.

DETAILED DESCRIPTION OF THE PREFERRED EMBODIMENT

Disclosed herein are systems, methods and apparatuses for monitoring the heath of a baby in utero. The system can include a strain sensor to measure the amount or frequency of movements of a fetus in the womb. The state of fetal health can be inferred by quantifying the frequency or amount of movement as an external health indicator. By continuously monitoring the movement, changes in the health of the baby can be sensed and the mother can be prompted to go to the hospital for medical supervision or urgent care. Importantly, the systems, methods, and apparatuses can measure fetal health indirectly and thus can be more quickly offered to mothers to provide information about the health status of their fetuses.

I. Fetal Health Monitoring System

Figure 1:
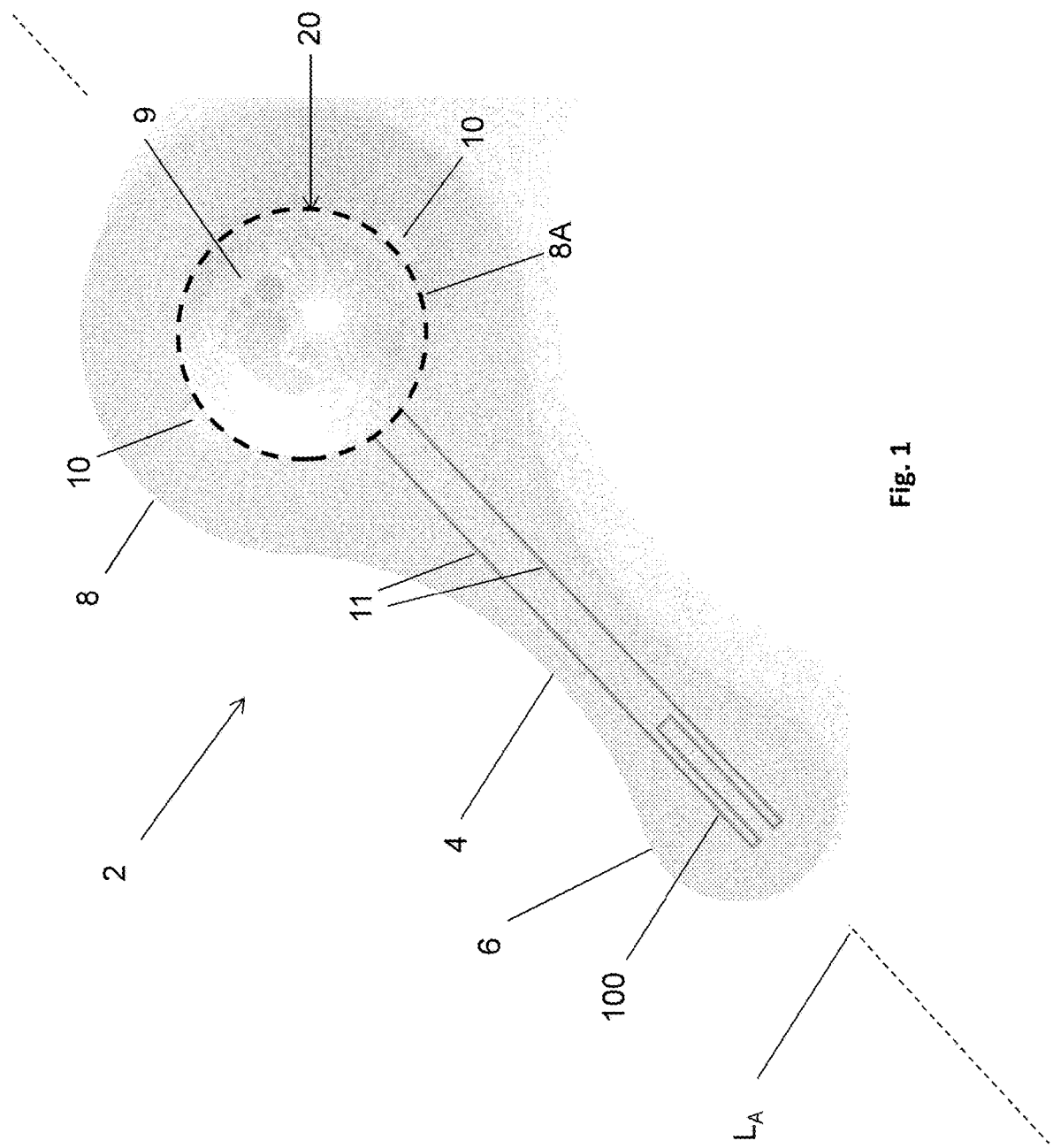
FIG. 1 shows a fetal health monitoring system that includes a disposable patient interface and a strain sensor.
Figure 2:
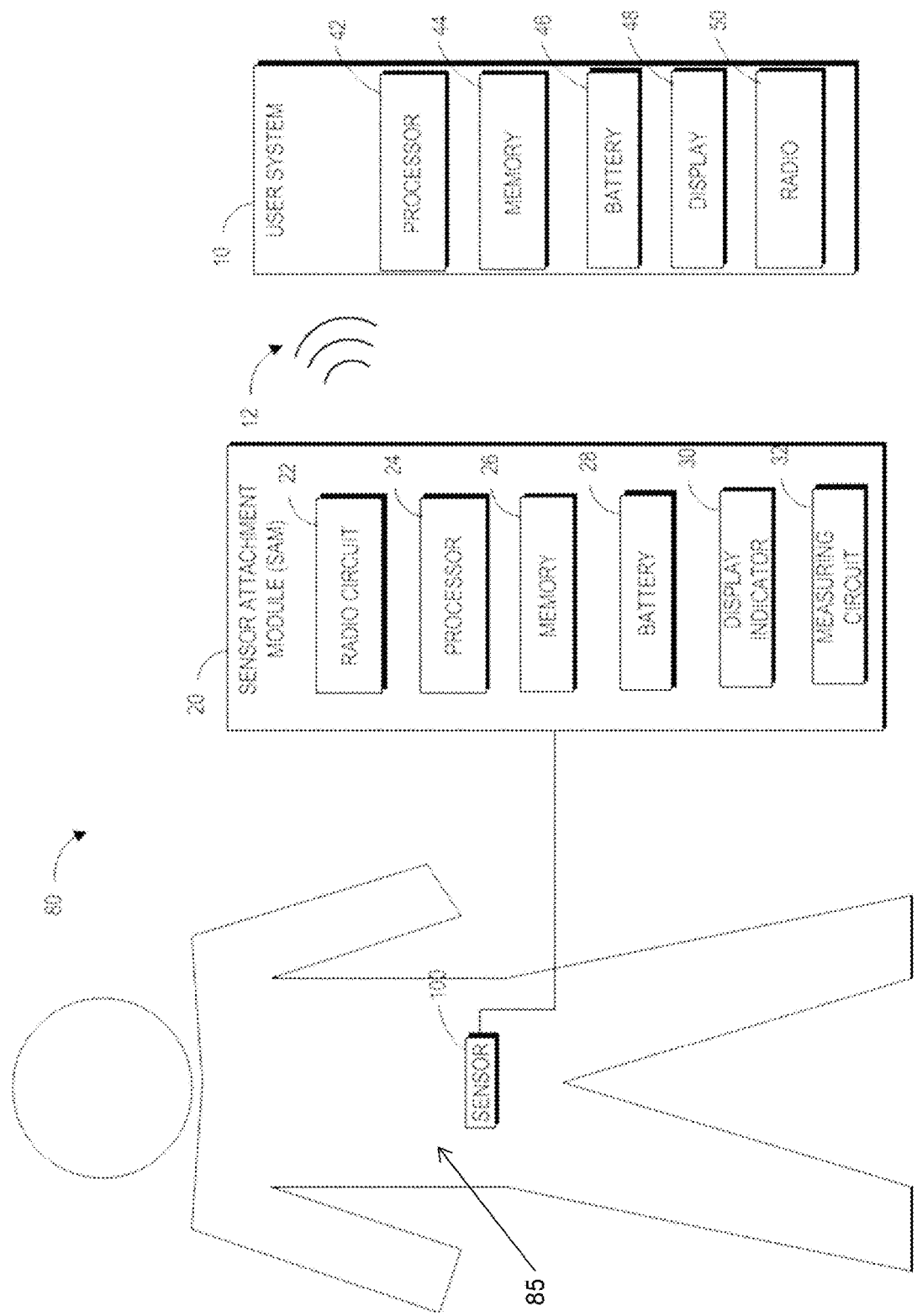
FIG. 2 shows a monitoring system including a wearable sensor, a sensor attachment module (SAM) and a pregnancy monitoring system (PMS).
Figure 3:
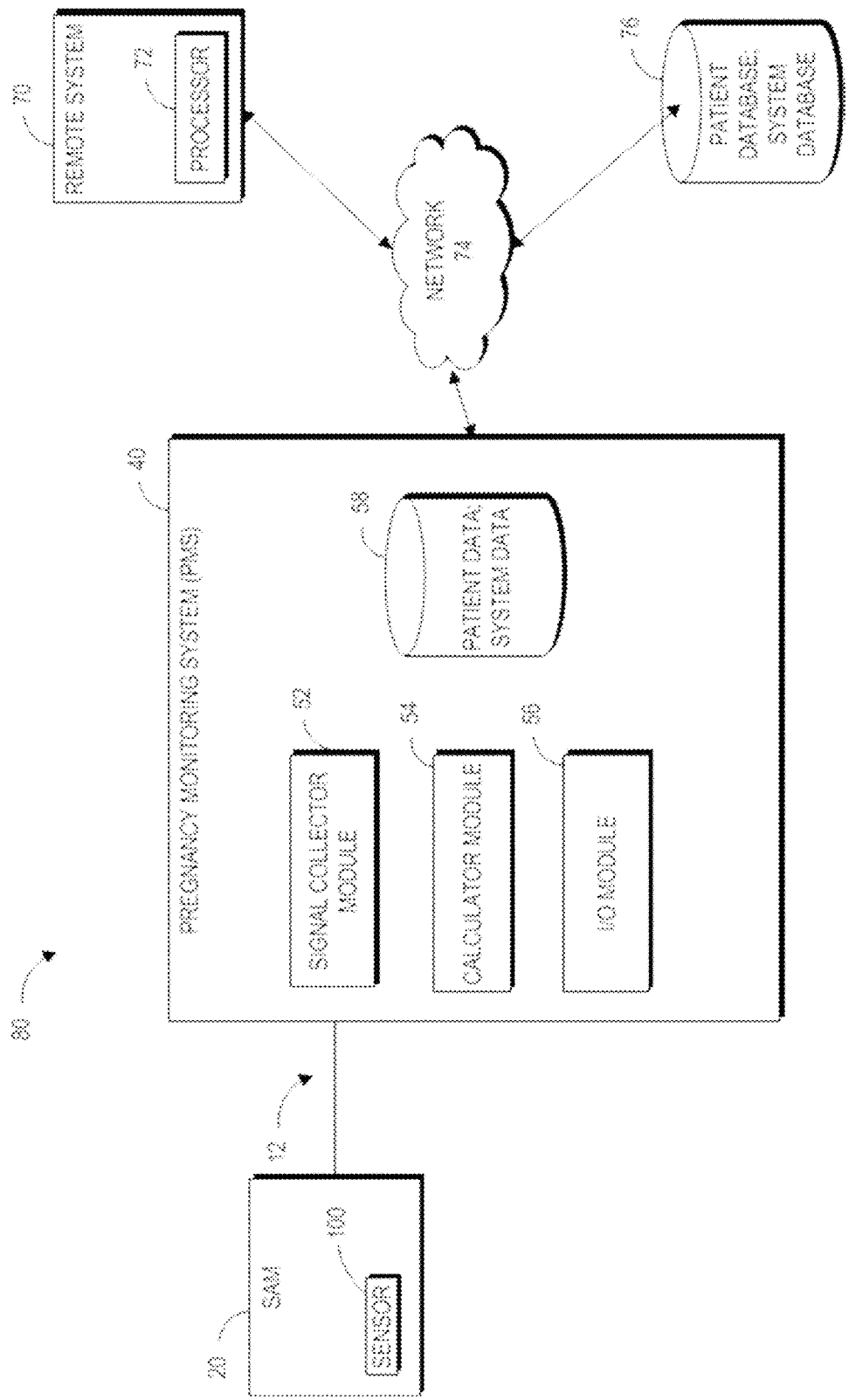
FIG. 3 shows the system of FIG. 2 connected through a network to a remote system and a database.

FIGS. 1-3 show embodiments of a system 80 for monitoring the health of a baby in utero. The system 80 can includes as one subcomponent a patient coupled portion 2 to be placed on the patient for a period of time from hours to days. The patient coupled portion 2 includes in one embodiment a sensor apparatus 100 and a sensor attachment module 20. The sensor apparatus 100 is adapted to be coupled directly to a patient, e.g., to the abdomen of a pregnant mother, as described in detail below. When so coupled, the sensor apparatus is conformal to the abdomen and is able to sense movements of the surface of the abdomen and of a baby in utero. The sensor apparatus 100 can be integrated into a flexible interface 4 that include a first side having an adhesive disposed thereon for connecting to the skin and a second side that is exposed.

The flexible interface 4 can have a first end 6 and a second end 8. The sensor apparatus 100 can reside at or in the first end 6. The integration of the sensor apparatus 100 into the flexible interface 4 can include disposing the sensor apparatus on or adjacent to a lower surface of the flexible interface 4. In one embodiment, the flexible interface 4 includes a thin and flexible fabric or plastic strip and a layer of adhesive and the sensor apparatus 100 is disposed on the lower surface of the flexible interface 4 between the strip and the adhesive. In another embodiment, a portion of the sensor apparatus 100 is coupled with the fabric or plastic strip but a portion that is configured to be sensitive to strain is only indirectly coupled with the fabric to prevent the movement of the strain sensitive portion from being constrained. In this way, the strain sensitive portion of the sensor apparatus 100 is isolated from and prevented from being stiffened by the flexible interface 4. In other embodiments, where the flexible interface 4 does not affect stiffen the strain sensitive portion of the sensor apparatus 100, the sensor apparatus can be disposed within the thickness of the flexible interface 4, e.g., spaced from both the lower and the upper surface of the fabric or strip portion.

The sensor attachment module 20 can be disposed at the second end 8. In one embodiment, the sensor attachment module 20 is configured as a reusable component and the sensor apparatus 100 and the flexible interface 4 are configured as disposable components. The sensor attachment module 20 has a housing 9 that encloses electronic components discussed below that receive and process the signals from the sensor apparatus 100. This allows the mother to remove the patient coupled portion 2 for certain activities, such as bathing or swimming if some portions of the system 80 are not water poof. To re-connect the system 80, the mother couples another flexible interface 4 with her abdomen and then makes a connection between the sensor and the sensor attachment module 20.

FIG. 1 shows by dashed line 8A that the second end 8 of the flexible interface 4 can have an annular shape. The annular shape in one embodiment provides an open area disposed inward of the dashed line 8A beneath the housing 9. The aperture can be configured such that the bottom of the sensor attachment module 20 is exposed to the skin when applied by the user. In another embodiment, the sensor attachment module 20 is just disposed above the flexible interface 4 so that there is a gap between the side of the flexible interface 4 not in contact with the skin and the bottom of the sensor attachment module 20. For example, the annular shape in another embodiment provide a thinner area of the material of the flexible interface 4 disposed inward of the dashed line 8A beneath the housing 9. The annular shape, e.g., open, thinner, or gap-defining area, allows the sensor attachment module 20 to loosely couple with the flexible interface 4. For example, an interface portion 10 can be provided on one or both sides of the sensor attachment module 20 to provide a mechanical and an electrical interconnect between the sensor attachment module 20 and the flexible interface 4.

By reducing the connection between the sensor attachment module 20 and the flexible interface 4 some mechanical isolation is provided between these components. This is advantageous in that the sensor apparatus 100 in certain embodiments includes a strain gauge which senses motion when under a strain. As such, motion and forces applied by the sensor attachment module 20 to the interface portion 10 are prevented from introducing a significant source of error in the strain gauge readings. Also, most of the mass of the patient coupled portion 2 is located in the sensor attachment module 20. By isolating this structure from the flexible interface 4 which is adhered to and conformal with the patient, comfort of the system is increased. Increasing patient comfort will enhance compliance with a monitoring regime.

Figure 10:
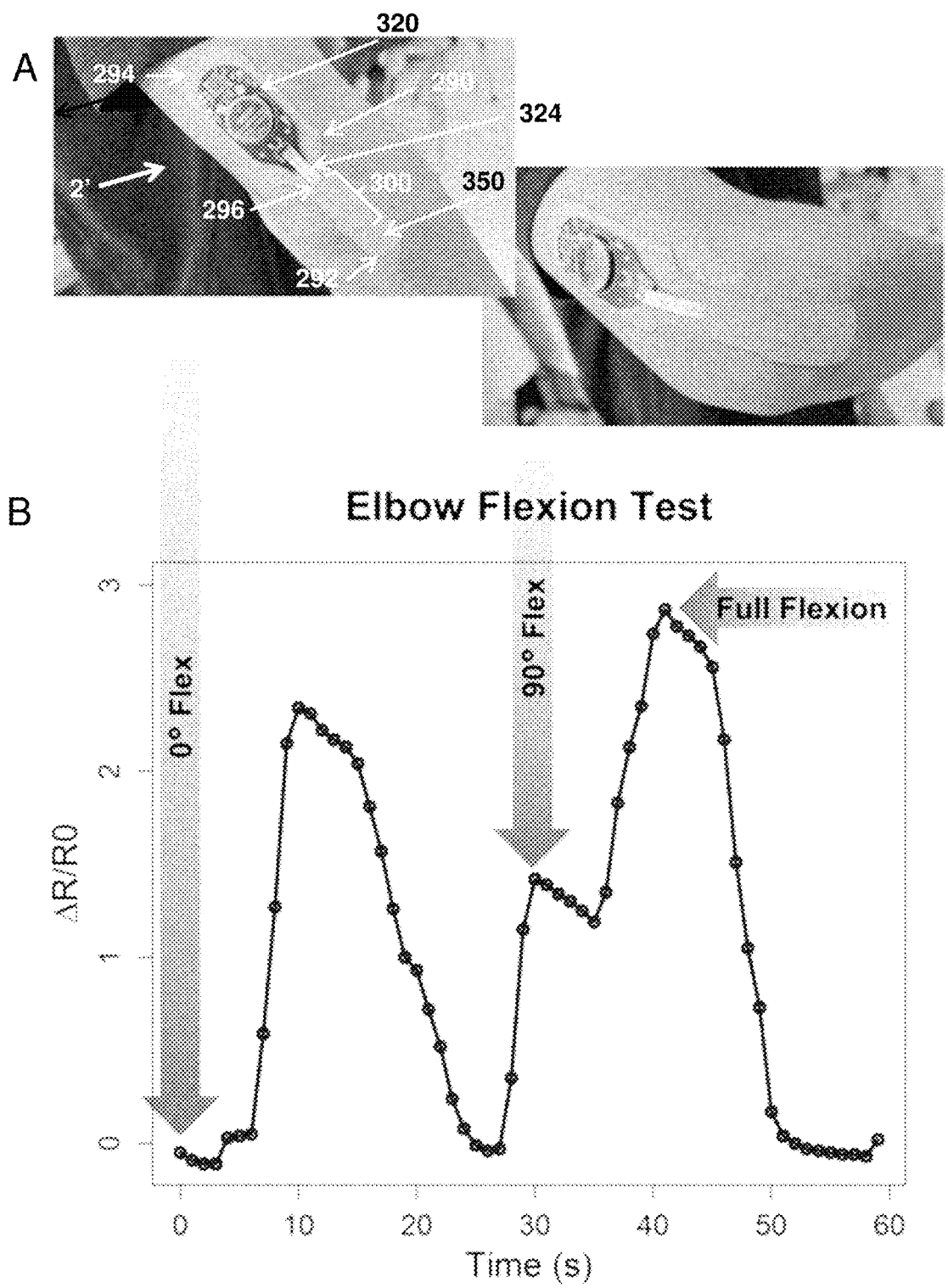
FIG. 10 (A) shows an assembly including a sensor apparatus and a sensor attachment module and shows an elbow flexion test that demonstrates the performance thereof.

An electrical connection 11 is provided between the sensor apparatus 100 and the sensor attachment module 20. The electrical connection 11 includes electrical traces that can have any suitable configuration. In some embodiments, the electrical connection 11 comprises one or more stretchable interconnect device 600 as discussed below in connection with FIGS. 15-19. The traces can be directly integrated into to fabric or plastic portion of the flexible interface 4 or can be disposed in another component, such as a flex cable as discussed below in connection with FIG. 10.

The flexible interface 4 is elongate between the first end 6 and the second end 8, extending along a longitudinal axis $L_A$ between the ends. In one approach, the flexible interface 4 is connected to the mother's abdomen transverse to the mid-plane of the body, for example with the end 6 disposed at or just above the belly button and the end 8 disposed laterally, to the right or left of the end 6.

Figure 4:
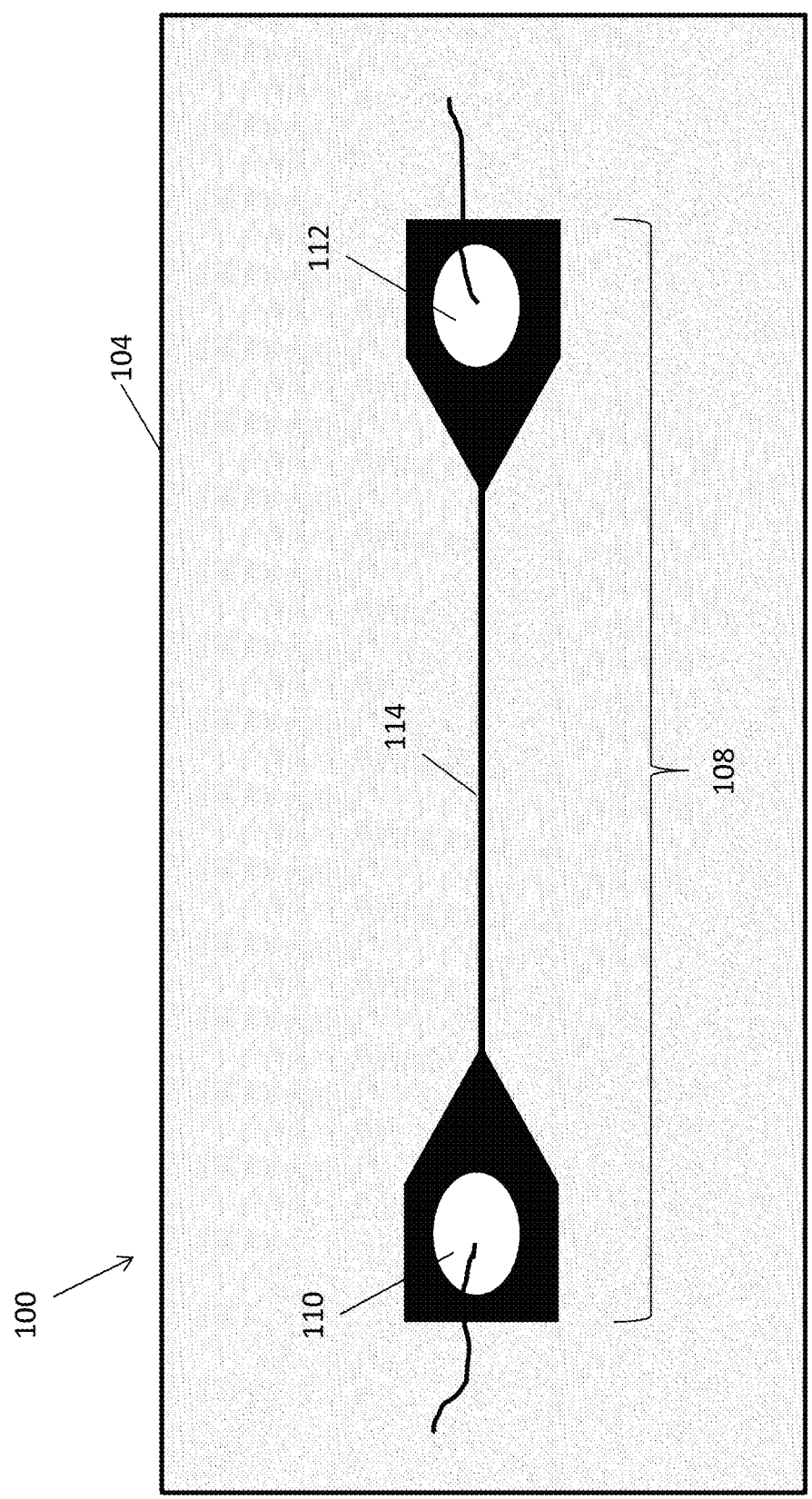
FIG. 4 depicts an embodiment of the wearable sensor of the system of FIG. 2, including a wrinkled metal film strain gauge.

As discussed above, the system 80 includes the sensor apparatus 100 described more in detail with respect to one embodiment in FIG. 4 that is well suited for a wide range of strain applications, including high strain applications. These characteristics make the sensor apparatus 100 well adapted for coupling with a pregnant mother and with the sensor attachment module 20. The sensor attachment module 20 is coupled by a flexible, moveable medium, e.g., the flexible interface 4 to be worn close to the uterus, e.g., on the abdomen near the bellybutton. In the case of a pregnant mother (reference number 85 in FIG. 1), the sensor attachment module 20 along with sensor apparatus 100 is to be worn on the abdomen and to respond to movements of the baby by generating a varying current signal.

Sensor Attachment Module

An embodiment of a sensor attachment module 20 is illustrated in FIG. 2. The sensor attachment module 20 can activate the sensor 100 and process signals received from the sensor 100. Activation of the sensor 100 can refer to measurement of a change in resistance of the sensor 100 using the measuring circuit 32. In some embodiments, the measuring circuit 32 includes a bridge circuit or any other circuit used for measuring a change in resistance in a strain gauge. The processor 24 can activate the measuring circuit 32 to sample the change in resistance over a period of time. The sampling frequency can be predetermined or dynamically change depending on patient data or a patient health event. For example, when the mother is having contractions, the system 80 may determine to increase sampling frequency. In the alternative, in some embodiments, if there are no changes in the mother, the system 80 may reduce sampling frequency to conserve an onboard battery 28. In one embodiment, the sampling frequency is 10 Hz.

The sensor attachment module 20 may also include a radio circuit 22 for transmitting data to a pregnancy monitoring system (PMS) over a link 12. In an embodiment, the PMS 40 receives the transmitted data via the user system 10. The link 12 may be wired or wireless. In some embodiments, the radio circuit 22 includes electronics such as an antenna for transmitting data using the Bluetooth protocol. Other transmission protocols, such as NFC, WiFi, or the like can also be used to transmit data from the sensor attachment module to the PMS. Transmitting data can be taxing on the battery 28 of the sensor attachment module. Accordingly, in some embodiments, the processor 24 determines when to transmit data to the user system 10. For example, the processor 24 can transmit data in response to a signal received from the user system 10 requesting transmission of data from the mother. The processor 24 can also process the received signal from the sensor 100 locally to determine whether the sensor data 100 needs to be transmitted to the PMS for further processing. Local processing may include comparing one or more characteristics of the signal with a stored threshold. The processor 24 can also be programmed to determine transmission of data based on a time of day or a pre-determined time interval. The signal data from the sensor 100 can be stored in the memory 26. In some embodiments, the transmitted data from memory 26 can be cleared to conserve space for storing additional data from continuous monitoring. In some embodiments, the system 80 provides a continuous 24 hour monitoring of the mother. Also, the size, shape, and weight of the sensor attachment module 20 may be constrained by concerns relating to long term wear-ability. Thus, in some embodiments, it may be advantageous to conserve battery power because a larger battery may not be feasible. In one embodiment, the sensor attachment module 20 is flexible.

The processor 24 can be programmed to determine whether the sensor 100 is properly attached to the sensor attachment module. In some embodiments, the sensor 100 may be disposable, while at least some portions of the sensor attachment module 20 may be reusable. Accordingly, a mother may be required to attach the sensor 100 to the sensor attachment module 20 on her own. Thus, in some embodiments, the sensor attachment module 20 can include a display indicator 30 for informing the mother that the sensor 100 is properly attached with the sensor attachment module 20. The display indicator 30 can include an LED or an LCD display.

Patient Monitoring System

The transmitted signals from the sensor attachment module 20 are received by the radio communication module 50 of the patient monitoring system (40). In general, the user system 10 and remote system 70 can include any type of computing device capable of executing one or more applications and/or accessing network resources. For example, the user system 10 and the remote system 70 can be desktops, laptops, netbooks, tablet computers, smartphones, smartwatches, augmented reality wear, PDAs (personal digital assistants), servers, e-book readers, video game platforms, television set-top boxes (or simply a television with computing capability), a kiosk, combinations of the same, or the like. The user system 10 and the remote system 70 can include software and/or hardware for accessing the PMS system 40, such as a browser or other client software.

An embodiment of the user system 10 including a block diagram of its hardware modules is illustrated in FIG. 2. For example, the user system 10 can include a hardware processor 42, a memory unit 44, a radio communications module 50, and a battery 46. In some embodiments, the user system 10 can also include a user interface display 48 for displaying results of monitoring and/or receiving input from a user.

FIG. 2 illustrates an embodiment of a pregnancy monitoring system (PMS) 40. The PMS 40 can be implemented in computer hardware and/or software. The PMS 40 can execute on one or more computing devices, such as one or more physical server computers, including for example, user system 10 and remote system 70. In implementations where the PMS 40 is implemented on multiple servers, these servers can be co-located or can be geographically separate (such as in separate data centers). In addition, the PMS 40 can be implemented in one or more virtual machines that execute on a physical server or group of servers. Further, the PMS 40 can be hosted in a cloud computing environment, such as in the Amazon Web Services (AWS) Elastic Compute Cloud (EC2) or the Microsoft® Windows® Azure Platform. The PMS 40 can also be integrated with SAM 20 or user system 10 through software or hardware plug-in or an API (application programming interface). In some embodiments, some or all of the modules of the PMS 40 may be implement by a user system 10 or a remote system 70, or a combination of both. For instance, the user system 10 may implement the I/O module 56, while the rest of the modules are implemented remotely on the remote system 70 running on a server. In other embodiments, a plugin to the PMS 40 may be installed on to a third party tool.

The PMS 40 includes a signal collector module 52 for receiving signals and performing initial processing. Initial processing may include reducing noise from the received signal. The PMS 40 can also include an I/O module 56 that can generate a user interface for displaying results. The user interface can be displayed on the user system 10. The user interface can also include controls that can enable users to input data. For example, a mother can enter input data using the user system 10 including the generated user interface from the I/O module. The user interface can also display trends or calendar of characteristics related to pregnancy. Characteristics can correspond to a number or frequency of contractions, kicks, or other aspects of motions associated with pregnancy. The user interface can also display indicia of the mother's pregnancy health. The indicia can include an alert informing the mother that it is time for her to go to the hospital.

The calculator module 54 of the PMS 40 can process received data from the sensor 100 to determine characteristics or indicia corresponding to the mother wearing the sensor 100. The calculator module 54 may implement machine learning algorithms for determining pregnancy parameters. The machine learning algorithms may be processor intensive. Accordingly, some of the functionality of the calculator module 54 described herein can be implemented remotely on a remote system 70. The user system 10 can transmit some or all of the received data to the remote system 70 over a network 74. The functionality of the calculator module is described more in detail with respect to FIGS. 21 and 22 below.

A. FLEXIBLE MINIATURIZED SENSOR APPARATUSES

Figure 12:
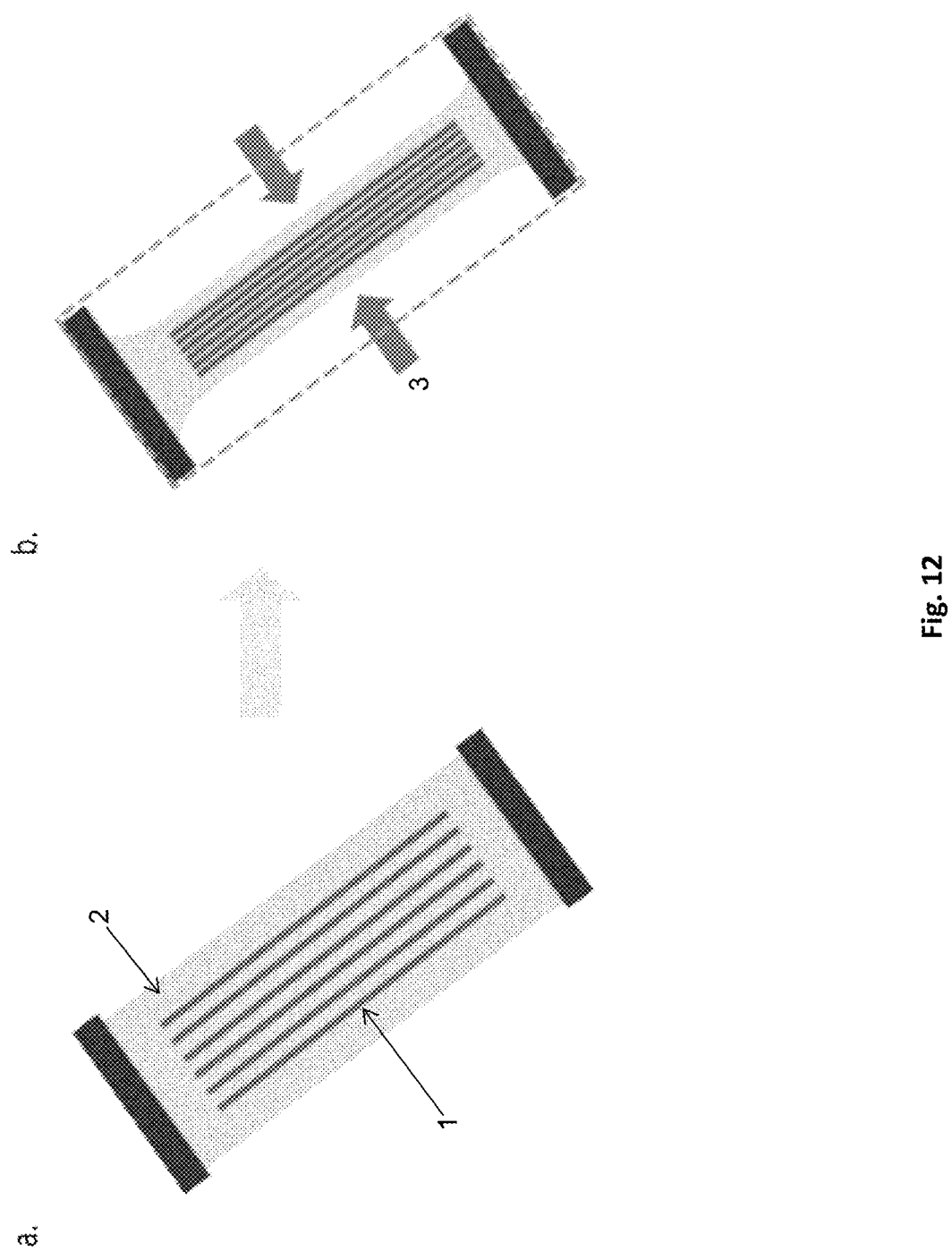
FIG. 12. Schematic of CNT densifying on polyolefin. (a) CNTs (1) on shape memory polymer, e.g., polyolefin (2), before shrinking. (b) CNTs on polyolefin after uniaxial shrinking (3) via heat resulting in densification.
Figure 13:
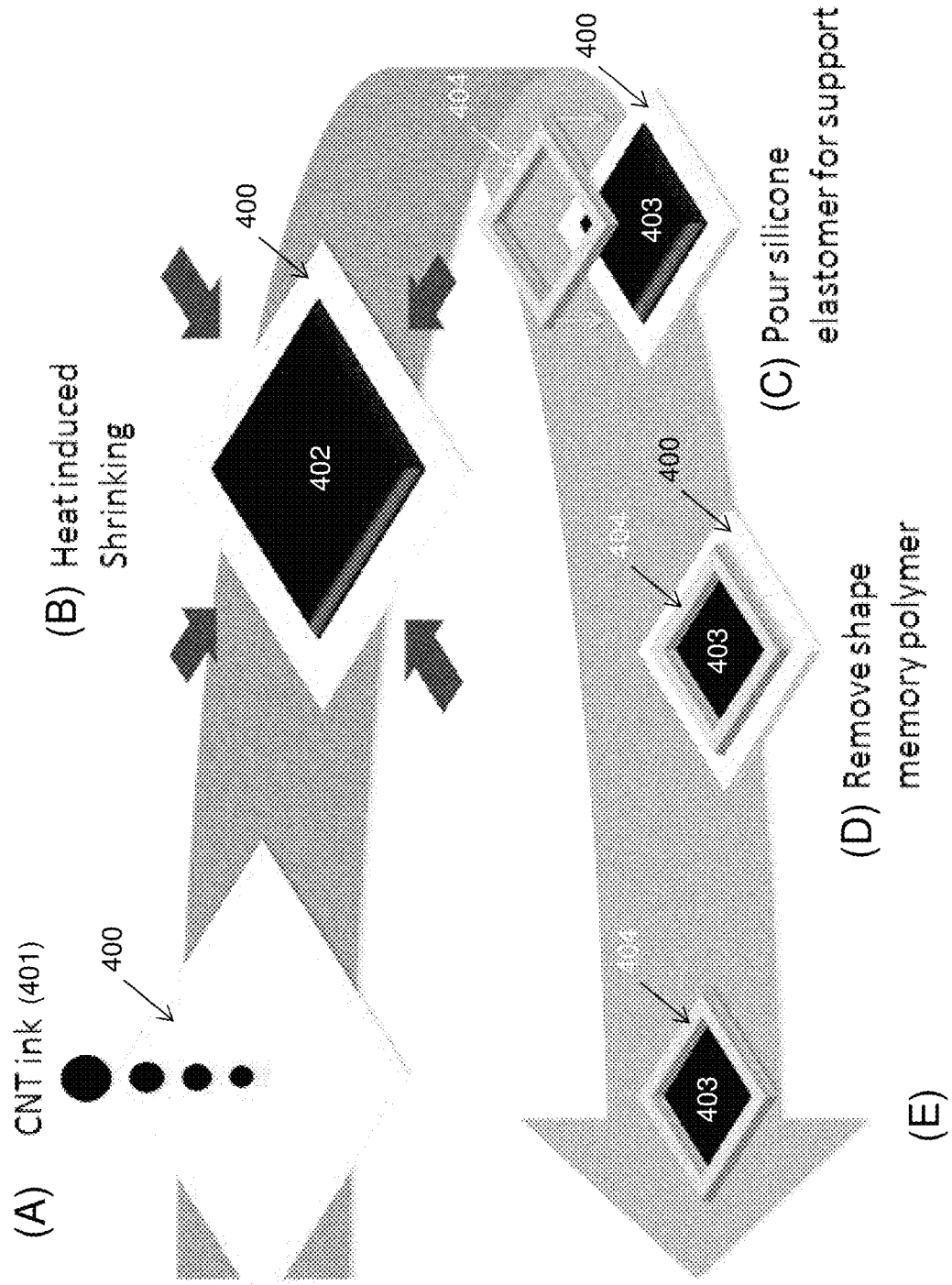
FIG. 13. Process flow for forming a wrinkled carbon nanotube (CNT) thin film. (A) Carbon nanotube ink is deposited on a flexible substrate; (9) Heat induced shrinking of preshrunk layer of CNT, resulting in shrunk CNT thin film; (C) Elastomer poured and cast onto shrunk CNT thin film; (D) Remove flexible substrate from shrunk CNT thin film and elastomer support; (E) shrunk CNT thin film with elastomer support.
Figure 14:
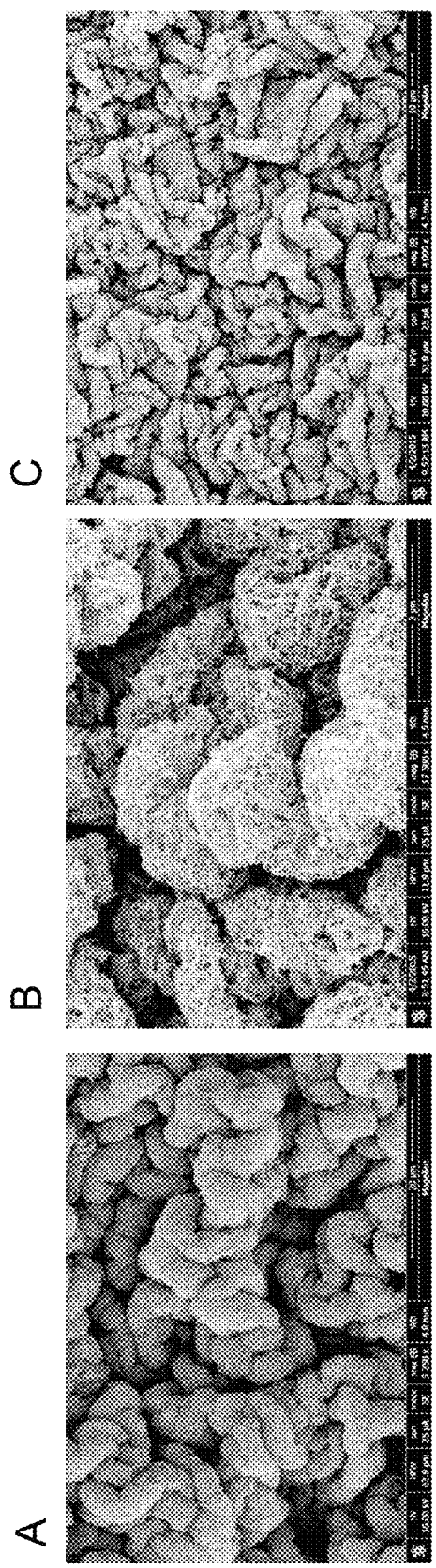
FIG. 14 show SEM images of wrinkled CNT thin film at various magnifications. (A) 3,250× magnification; (B) 17,500× magnification; and (C) 4,000× magnification.

FIGS. 4-15 illustrate a variety of structures that can be incorporated into the sensor apparatus 100 to reliably detect a fluctuating signal, such as a detectable change in resistance, for motion detection in a disposable wearable sensor. FIGS. 4-11 illustrate thin film metal strain gauges, FIGS. 12-14 illustrate one-dimensional structures, including nanotubes and nanowires for use as disposable wearable strain gauge sensors.

1. Sensors Having a Metal Film Conductor

Figure 5:
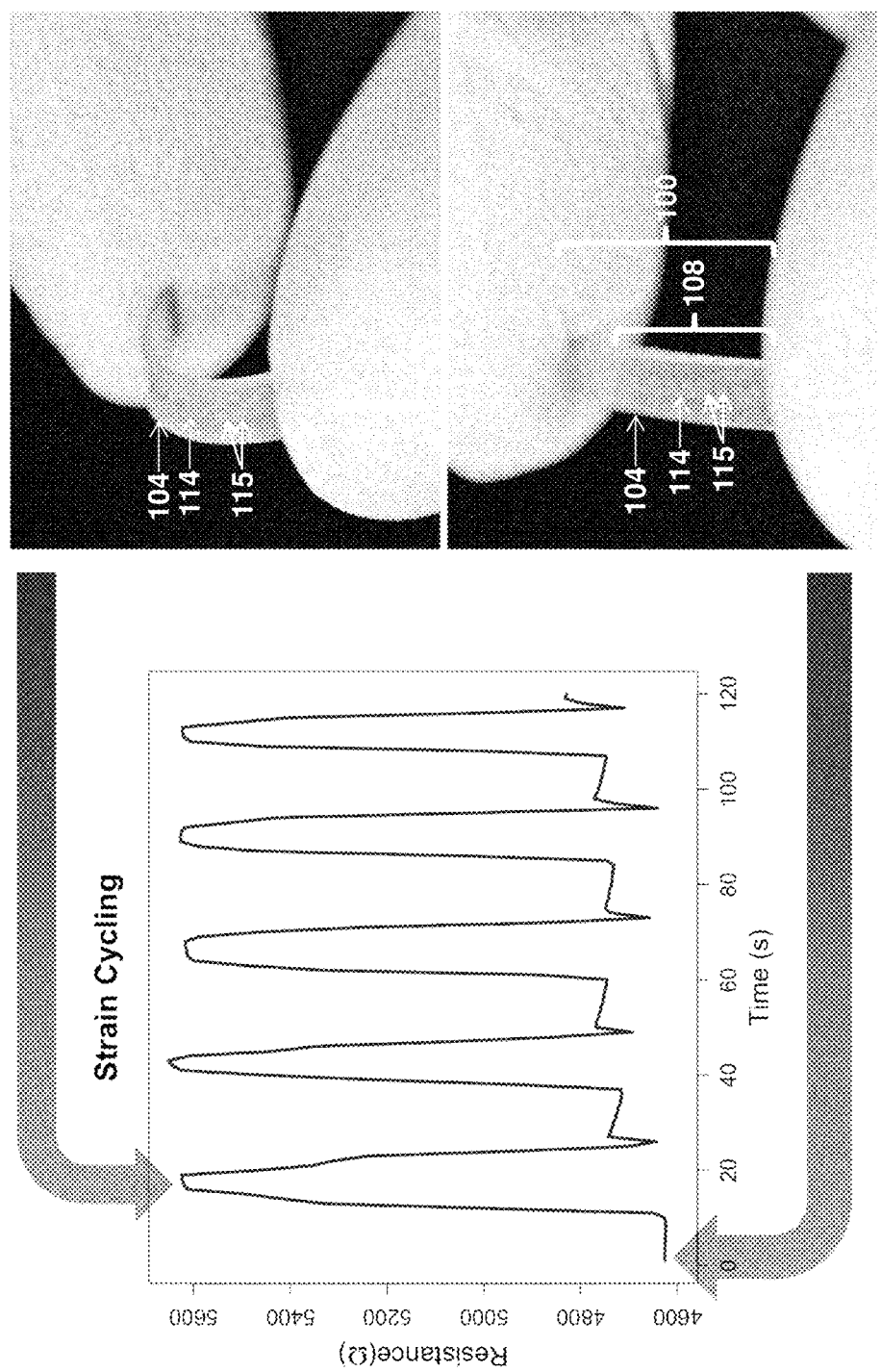
FIG. 5 shows the resistance response of a wrinkled metal film strain gauge. Resistance peaks correspond with maximum strain of 5%. The bottom arrow indicates the initial, unstrained resistance of the wrinkled metal film strain gauge.
Figure 16:
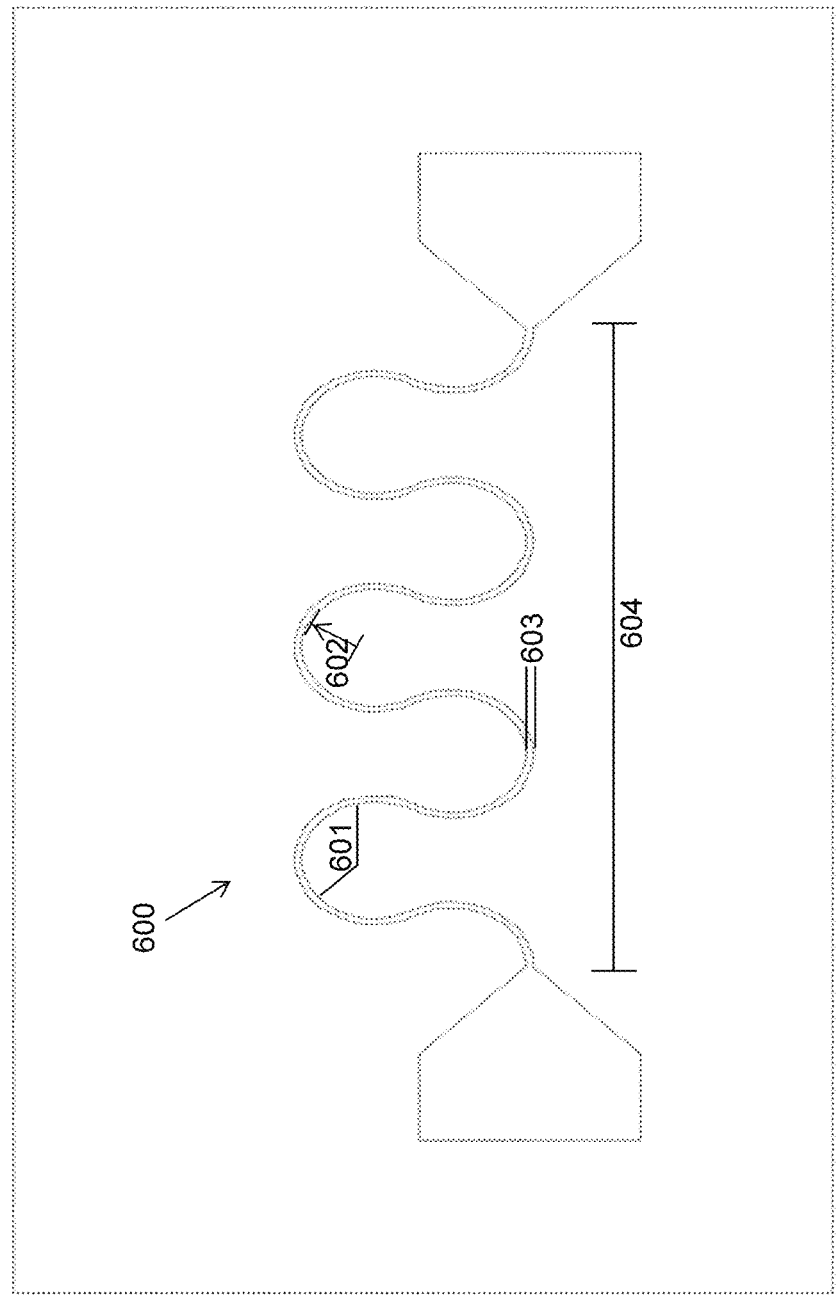
FIG. 16 illustrates a serpentine geometry of a stretchable interconnect that can be used in the system of FIG. 1.
Figure 17:
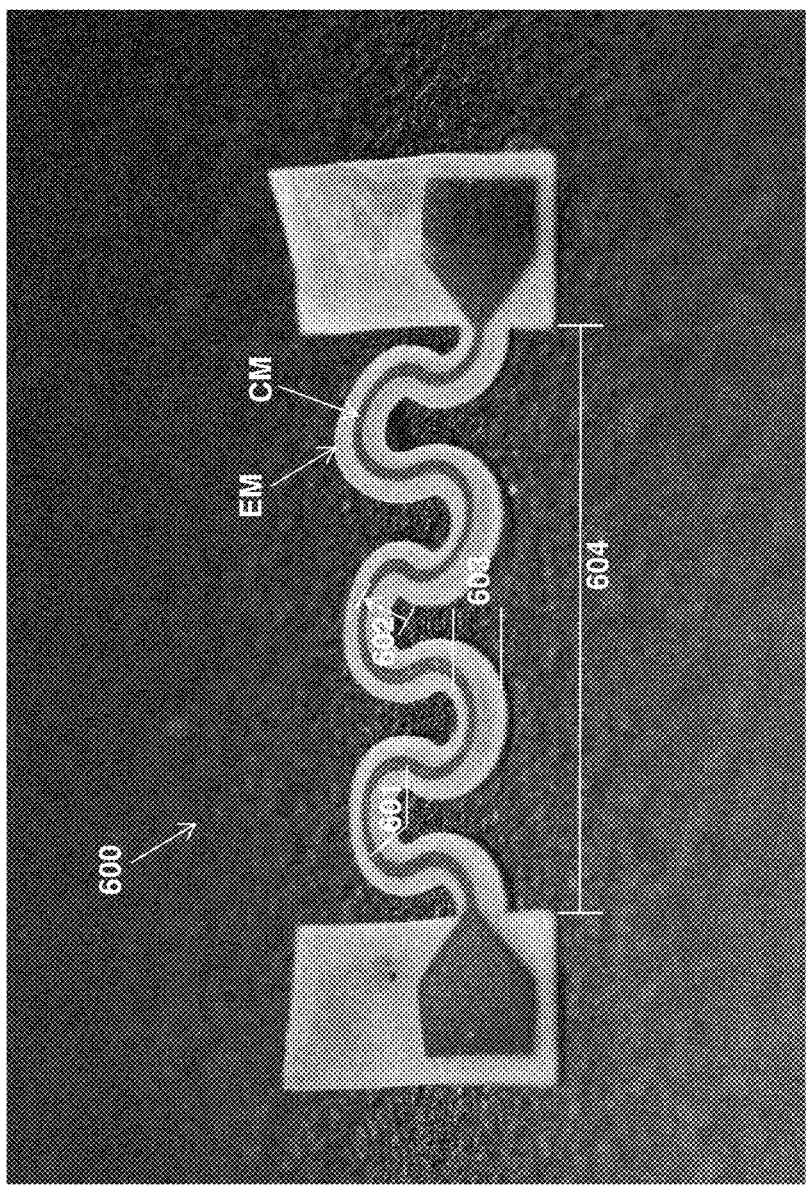
FIG. 17 shows a an embodiment of a stretchable conductive interconnect.
Figure 18:
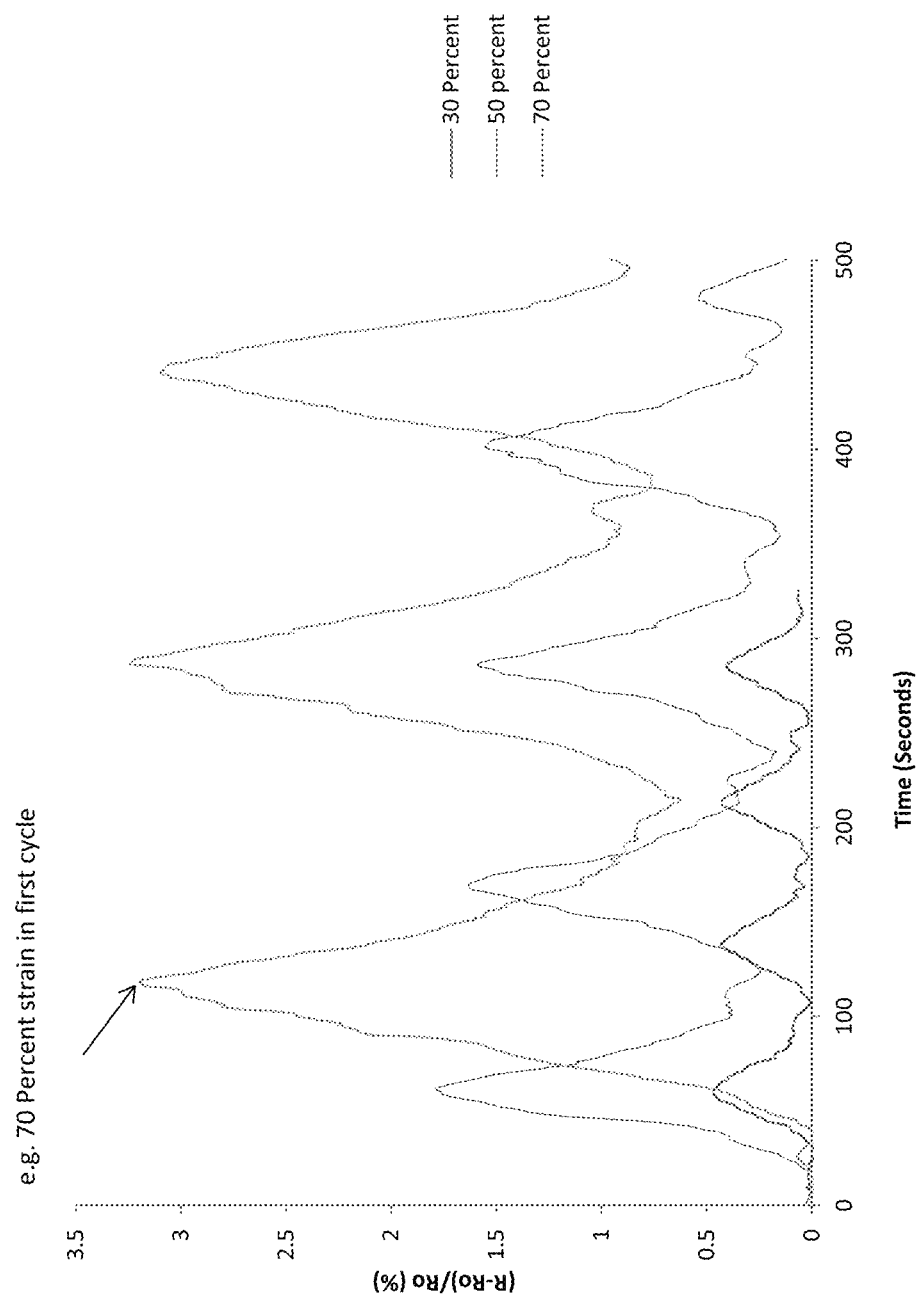
FIG. 18 shows electrical signals in cycling of a stretchable interconnect at different strains.

In one embodiment, as depicted in FIG. 4, the sensor apparatus 100 includes a flexible substrate 104 and a conductor 108. In the illustrated embodiment, the conductor 108 initially is formed as a thin metal film but thereafter crumpled or wrinkled because the material it is formed upon is shrunk to a fraction of its initial size. A plurality of electrical contacts 110 and 112 are in electrical communication with the conductor 108. The electrical contacts 110, 112 can be disposed at opposite ends of an elongate conductive region 114. In other embodiment, more than two contacts can be provided. For example, FIG. 5 shows one modified embodiment in which a plurality of contacts 115 are disposed along the length of an elongate conductive region 114 on flexible substrate 104. The contacts 115 in this embodiment are disposed to one side of the elongate conductive region and allow connection to other devices at a number of different positions and/or permit a number of different devices to be in contact with the elongate conductive region. For example, any two of the contacts 115 can be used to measure a signal such as current or a change in a property such as resistance at a location along the conductive region 114. FIGS. 16 and 17 show embodiments of a stretchable lead structure that can be incorporated into a sensor apparatus, for example attached to conductive region 114 or to contacts 110, 112, 115 or to leads connected to the contacts 110, 112 as discussed below.

Figure 6:
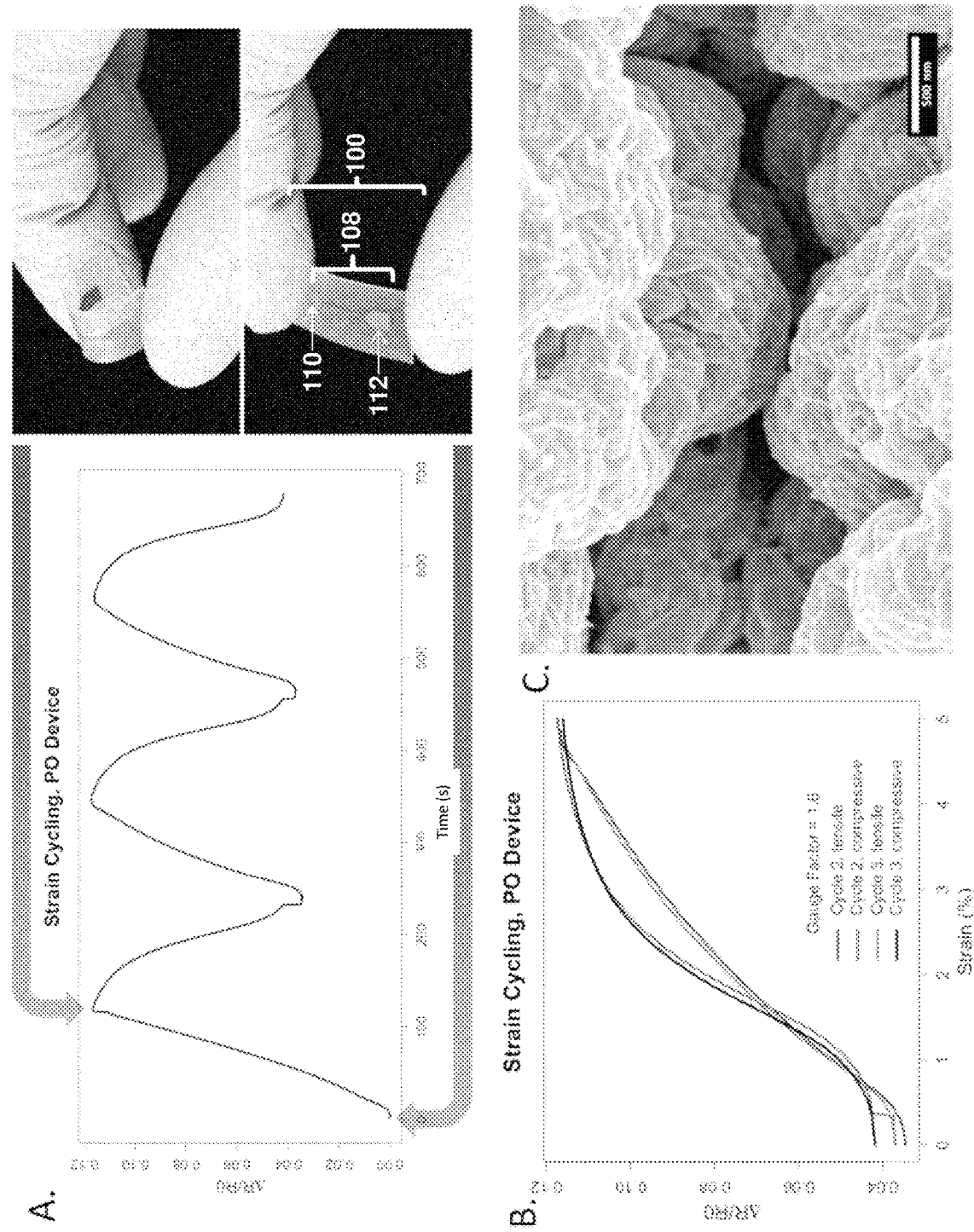
FIG. 6 shows strain cycling of a wrinkled metal film strain gauge. Panels (A) and (B) show semi-static linear strain cycling. Panel (C) is a top down scanning electron micrograph (SEM) of adjacent wrinkles in contact.

The sensor apparatus 100 is able to undergo very high strain, which induces a detectable change in a signal as illustrated in FIGS. 5 and 6. The signal can be a change in resistance.

One configuration that enables high range of strain is the physical configuration of the film conductor 108. In particular, as shown in FIG. 6(C), at the micron-scale the conductor 108 is not flat but rather is crumpled or wrinkled. This configuration can exhibit secondary folding in some embodiments. Non-shrunk and shrunk electrodes have a linear decrease in resistance across patterned line electrodes of different widths. Measuring electrical resistivity before and after the thermal shrinking process shows a dramatic improvement in electrical conductivity of wrinkled Au thin film electrodes over the non-shrunk, planar Au electrodes. Cross-sections of the wrinkled metal films reveal many tens of micron-scale invaginations in the surface where adjacent wrinkles pack closely enough that they begin to coalesce, referred to as secondary folding. In a flat metal thin film, discontinuities produce a large effect in the resistivity of the film. Without wishing to be bound to any particular theory, we hypothesize that secondary folding in a wrinkled Au thin films creates an increase in electrical contacts, thereby circumventing these discontinuities and reducing the effective resistivity of the wrinkled thin film electrodes.

Moreover, the crumpled configuration of the conductor 108 allows for a great degree of extensibility when subject to strain. The conductor 108 is folded upon itself in the at-rest state and unfolds or unfurls when under strain to an elongate state without being subject to fracture. This mechanical integrity allows the conductor 108 to continue to function even when under strains that are severe for conventional thin film strain gauges.

a. Method of Forming High Strain Film Conductor

Figure 7:
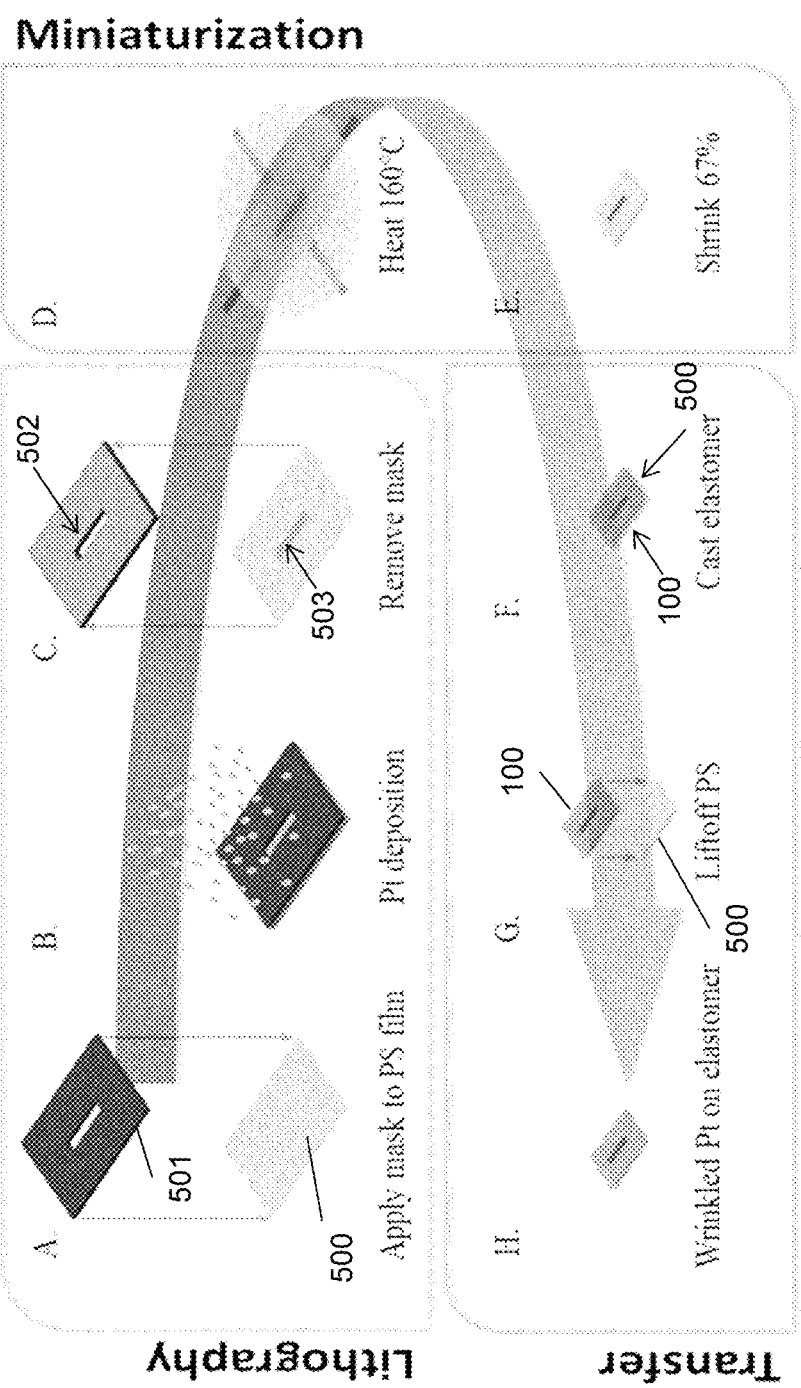
FIG. 7 illustrates a process for making and transferring a wrinkled metal thin film to an elastic material. The process can be separated into 3 sub-processes: Lithography (A-C), Miniaturization (D, E), and Transfer (F-H).

The micron-scale configuration discussed above can be provided by any suitable method. FIG. 7 shows one technique that involves exploiting a heat-shrink material. In FIG. 7, panel (A) the polystyrene shrink film is masked. In panel (B) a metal thin film is deposited, in panel (C), the mask is removed and in panels (D and E) the shrink film is heated to 160° C., shrinking the metal patterned polymer by about 67% by surface area. In panel (F), a flexible polymer, such as ECOFLEX 30™, is spin coated onto the shrunken sample and cured. In panel (G), a series of solvent baths or other separation technique is used to lift off the polystyrene, resulting in the wrinkled metal thin film transferred onto the silicon elastomer (panel H). In some embodiments, a polymeric sheet 500 of suitable heat-shrink characteristics is placed adjacent to a mask 501 configured to block regions of the polymeric sheet 500. This may be followed by a step of depositing a conductive structure 503 on the polymeric sheet 500 at regions exposed through the mask 502. After the conductive structure 503 is formed, the mask 501 can be removed. The process then follows with shrinking the polymeric sheet 500 with the conductive structure 503 patterned on its surface by heating. The metal-patterned polymer may be reduced in size with regard to surface area by 5%, 10%, 15%, 20%, 25%, 30%, 35%, 40%, 45%, 50%, 55%, 60%, 65%, 70%, 75%, 80%, 85%, 90% or 95%. Thereafter, the conductive structure 503 is transferred to a flexible substrate.

The conductive structure 503 can be deposited by any method, for example by air brushing or by electrospray of a material onto a surface. In some embodiments, the conductive structure 503 comprises any conductive metal. In some embodiments, the metal conductive structure is a thin metal film. In some embodiments the metal is selected from the group consisting of Cu, Ag, Au, and Pt. In some embodiments, the polymeric sheet 500 may be a shape-memory (e.g., a shrink-wrap) polyolefin (PO) film. The shrinking step may performed at a temperature of about 100° C., 110° C., 120° C., 130° C., 140° C., 150° C., 160° C., 170° C., 180° C., 190° C., 200° C. 210° C. or 250° C. Among the materials that are well suited for heat-shrink processing is polystyrene.

b. Sensor Assembly Including a High Strain Film Conductor and Flexible Medium

The foregoing method forms a suitable conductive structure for a sensing apparatus. However, many heat shrink materials are more rigid than would be preferred for some applications. For example, it may be desirable to configure the sensing apparatus with as little shape-retaining characteristics as possible. It may be desired to permit the sensing apparatus to drape over a natural structure such as a joint or an expanse of skin. It may be desirable to couple this highly conformal sensing apparatus to a platform that will retain mechanical integrity during continuous use of an hour or more, up to two hours, or even a period of twenty-four hours or more. Thus, it may be desired to transfer the conductive structure to a flexible substrate. The flexible substrate can provide mechanical backing for the highly conformal sensing apparatus while allowing it to retain sufficient flexibility to reliably and repeatedly detect movement.

In one method, it is desired to transfer the conductive structure 503 to an elastomeric polymer. One technique involves cast molding an elastomeric polymer support 504 onto the same surface of a heat-shrunk polymeric sheet 500 upon which the conductive structure 503 is deposited (see FIG. 7, step F). The cast molding can involve preparing the elastomeric material in liquid form and dispensing it onto the surface upon which the conductive structure 503 is deposited. The liquid elastomeric polymer is permitted to solidify. Thereafter, the conductive structure 503 is sandwiched between an elastomeric layer of the support 504 and the heat-shrunk polymeric layer 500. Thereafter, the heat-shrunk polymeric layer 500 optionally is removed (see FIG. 7, step G), leaving the conductive structure 203 on the surface of the elastomeric layer of the support 504.

Metal patterns can be fabricated directly on polydimethylsiloxane (PDMS) by using stencil masks or photolithography; however, there are some limitations to these methods, such as being restricted to patterns with only simple structures, contamination by wet chemicals and cracks because of a large mismatch in the coefficient of thermal expansion of PDMS and that of metals. More importantly, after direct metal patterning on PDMS, high-temperature processes (e.g., annealing) cannot be applied to the sample because of the low melting point of PDMS. Instead of direct-metal patterning on PDMS, it has been reported that metal patterns can be prepared on rigid substrates (e.g., Si or glasswafer); and then the patterns can be transferred to receiver substrates (e.g., PDMS).

For flexible electronics, a strong bond between the metal and the PDMS substrate is very important in order to fabricate a robust and reliable device that is able to endure the stresses induced by the bending of the substrates. If the metal patterns do not bond strongly to the PDMS surface, they can be damaged or lifted off easily by the applied voltage or fluidic pressure. For example, evaporated Au does not adhere to PDMS due to the weak interaction to PDMS.

An adhesion layer is optionally placed between the conductive structure and the elastomeric layer. In some embodiments, Pt is deposited first on a polymeric material, such as polystyrene (see FIG. 7, step B). This may be followed by deposition of a thin layer of Au, which forms metallic bonds with the Pt. Any silane molecule may be used as a surface adhesion molecule. For example, when silicon polydimethylsiloxane (PDMS)) is used as the elastomer, the thin film of Au can be covalently bonded to the silicon elastomer using 3-mercaptopropyl) trimethoxysilane (MPTMS) as a molecular adhesive (Byun I. et al. 2013 J Micromech Microeng 23(8): 1-10, incorporated herein by reference). Following heat-shrinkage of the polymeric material (see FIG. 7, steps D and E), the gold surface is treated with 3-mercaptopropyl) trimethoxysilane (MPTMS), which functions as a molecular adhesive in bonding the conductive layer to the silicon elastomer. When the wrinkled, conductive layer attached to the elastomer is lifted off of the heat-shrunk polymer, the Pt is exposed.

Several methods to promote adhesion between metal patterns and PDMS are known. The first is to use Ti or Cr as an adhesion interlayer and then activate and hydroxylate the respective surfaces of the metal and PDMS by oxygen plasma or UV/$O_3$ exposure in air. Conformal contact of two hydroxyl (—OH) groups on Ti (5 nm) surface (titanol) and hydroxylated PDMS surface (silanol) by oxygen plasma treatment results in permanent Ti—O—Si bonds. Cr (3 nm) and $SiO_2$ (30 nm) can be deposited on Au electrodes and delivered to PDMS, which is surface activated by exposure to UV/$O_3$, to form Si—O—Si linkages. Similarly, the adhesion can be enhanced between the metal electrodes and the PDMS by thermal curing a prepolymer of PDMS on Au electrodes with Ti interlayer (5 nm). However, using Cr or Ti as an adhesive layer can deteriorate the optical and electrochemical performance of the device, nor are these elements suitable for bio-applications. However, using a molecular adhesive that bonds to both the metal and PDMS may be an alternative to avoid the problems caused by additional metallic interlayers.

For a molecular adhesive, (3-mercaptopropyl) trimethoxysilane (MPTMS), as a self-assembled monolayer (SAM), is versatile because of the different functionality of its two terminal groups. Simultaneously, the three methoxy (—$OCH_3$) functional end groups can bind to oxide surfaces, while the thiol (—SH) functional head group can bind to metals. MPTMS has been used for the transfer of Au films to PDMS. Au patterns treated with MPTMS can bond to PDMS by pouring a PDMS prepolymer onto the Au patterns and subsequent thermal curing or bringing the Au patterns to PDMS whose surface was activated by exposure to UV/$O_3$. Not only Au, but also PDMS can be treated with MPTMS. This PDMS treated with MPTMS can bond with Au patterns by bringing them into contact.

Other alternative polymer elastomers may be used, such as urethane. For other types of polymer elastomers, corresponding adhesion methods are utilized.

The presence of an adhesion layer that adheres the conductive structure to the elastomeric substrate can significantly improve the dynamic range of a sensor. Without wishing to be bound to any particular theory, this may be because the conductive structure is anchored to the elastomeric substrate, allowing it to stretch in response to strain and to retract to its original conformation upon relaxation of the strain. In some embodiments, the dynamic range of a sensor containing an adhesion layer interposed between the conductive structure and the elastomeric layer is 10%, 20%, 30%, 40%, 50%, 60%, 70%, 80%, 90%, 100%, 110%, 120%, 130%, 140%, 150%, 160%, 170%, 180%, 190% or 100% greater than a comparable sensor that lacks an adhesion layer.

Further steps may involve encapsulating the conductive layer. Further steps may involve coupling the conductive layer with other devices, such as may be used to direct current through the conductive layer, to receive current directed through the conductive layer, to store and/or transmit data regarding the resistance or changes in resistance of the conductive layer, to provide one or more signals to the user or patient or for other purposes.

FIGS. 8, A and B show mechanical integrity tests for an embodiment of the sensor apparatus 100. The sensor apparatus 200 includes the contacts 110, 112 which can be coupled with electrical conductors C as shown. The ends of the apparatus 100 are illustrated as being coupled with a pull test apparatus. The pull test apparatus pulls the ends of the apparatus 100 away from each other. In the test illustrated, current was caused to flow in a pulled state (panel B) through the sensor apparatus up to a strain of at least 150%. In at least one test a strain of 900% in a pulled state (panel B) was attained to show that the sensor apparatus 100 is able to stretch to a very high degree and still retain its overall structural integrity.

Figure 9:
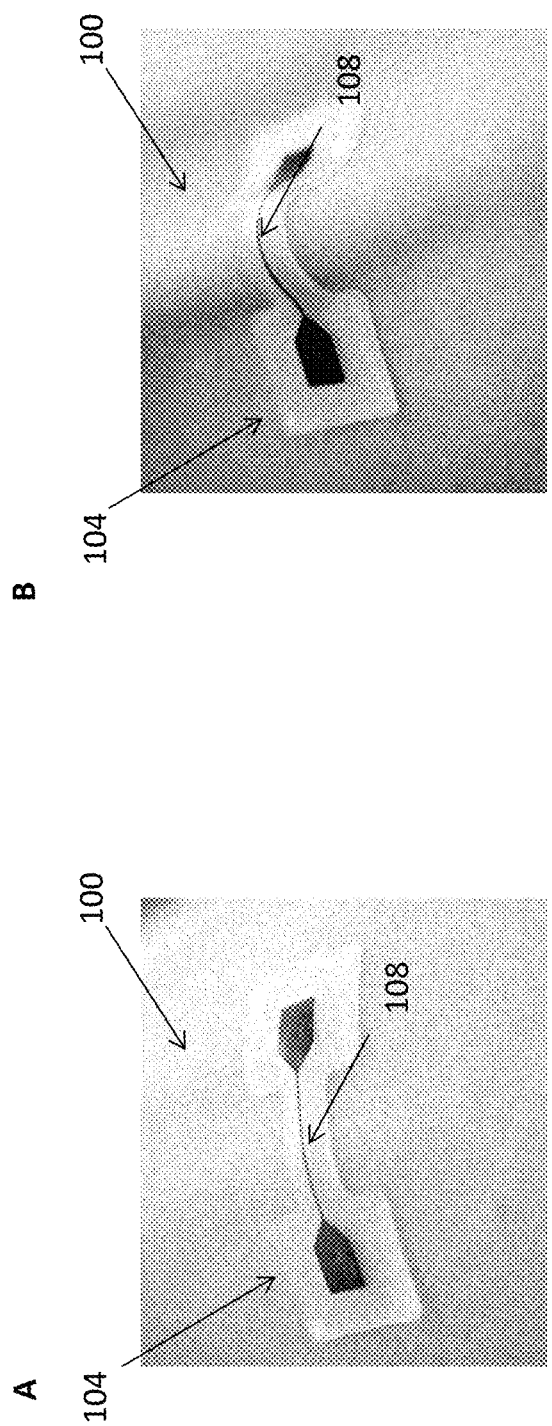
FIG. 9 (A and B) show conformability of an embodiment of a sensor apparatus according to the methods herein.

FIGS. 9, A and B show gross mechanical characteristics of the sensor apparatus 100. The sensor apparatus 100 is very flexible and can be draped over a skin structure. The sensor apparatus 100 includes the thin film conductor 108, which is embedded in the flexible substrate 104. The flexible substrate 104 can at least partially encapsulate the thin film conductor 108. Panel A shows a rest state of the sensor apparatus 100 and the skin. Panel B shows a flexed state of the skin. That is, in this test the skin is gathered at a location spaced away from but close to the sensor apparatus 100. The gathering pulls the skin together, causing the ends of the apparatus 100 to move closer together. In this test, the ends move closer together with the skin. The sensor apparatus 100 is flexible so that the skin will return to the state of panel A after being moved to the position of panel B. The flexibility of the flexible substrate 104 is useful in that it helps to maintain the sensitivity of the thin film conductor 108 to the conditions to be sensed.

FIG. 10A shows another embodiment of a patient coupled portion 2' and FIG. 10B shows changes in resistance (ΔR/Ro) as a function of strain sensed by a sensor apparatus 300. The patient coupled portion 2' includes a flexible interface 290. The flexible interface 290 includes a first end 292 and a second end 294 disposed on an end of the interface opposite the first end 292. The second end 294 is wider such that it can accommodate a sensor attachment module 320. The sensor attachment module 320 can be disposable or reusable.

The flexible interface 290 preferably includes an aperture 296 disposed along the length thereof between the first end 292 and the second end 294. The aperture 296 is configured to permit a sensor apparatus 300 to be inserted therethrough. When so inserted, the sensor apparatus 300 is located at or adjacent to the first end 292. The sensor apparatus 300 can be entirely disposed under and/or be covered by the expanse of the flexible interface 290. In one embodiment, signals are conveyed from the sensor apparatus 300 to the sensor attachment module 320 by a flex circuit 324 that is extends between the sensor apparatus 300 and the sensor attachment module 320. The flex circuit 324 can include a ribbon cable or assembly of a conductor disposed in a flexible, e.g., polymeric, sheet.

In one embodiment, the sensor apparatus 300, flex circuit 324 and sensor attachment module 320 are provided as an assembly. To apply the patient coupled portion 2', the patient threads the sensor apparatus 300 and the flex circuit 324 through the aperture 296 to dispose the sensor apparatus 300 beneath the flexible interface 290 in direct contact with the user's skin, e.g., directly on the skin of the abdomen just above the belly button. The flexible interface 290 can have an adhesive adapted for coupling with the skin at both the first end 292 and the second end 294. In one embodiment, the first end 292 has a central area in which the sensor apparatus 300 is disposed. The central area can be configured to minimize or reduce the tendency of the flexible interface 290 to create a source of error in the sensor output. For example, if the sensor is a strain gauge the central area can be configured to not have adhesive so that the sensor apparatus 300 can be trapped between the skin of the mother and the flexible interface 290 but not be rigidly adhered to the interface.

In one embodiment, the sensor attachment module 320 is disposable and can be shipped coupled with the flexible interface 290. After use, the sensor attachment module 320 and the flexible interface 290 can be disposed of. In another embodiment, the sensor attachment module 320 is reusable and is configured to be releasably coupled with the flexible interface 290. For example, the sensor attachment module 320 can be coupled and shipped with the flexible interface 290 but can be removed therefrom and reattached by the user to another the flexible interface 290. In one arrangement where the sensor attachment module 320 is reusable, the sensor apparatus 300 can be provided in an assembly with the flex circuit 324. In such arrangement, the flex circuit 324 and the sensor attachment module 320 preferably have connectors enabling the user to electrically couple the flex circuit 324 to the sensor attachment module 320.

FIG. 13 shows a process flow for forming a wrinkled carbon nanotube (CNT) thin film. In panel A, carbon nanotube ink 401 is deposited on a flexible substrate 400. In panel B, heat induced shrinking of preshrunk layer of CNT 402 results in shrunk CNT thin film 403. In panel C, elastomer 404 is poured and cast onto shrunk CNT thin film 403. In panel D, flexible substrate 400 is removed from shrunk CNT thin film 403 and elastomer support 404. Panel E shows shrunk CNT thin film 403 with elastomer support 404.

2. Sensors Having a One Dimension Nanostructure

In some embodiments the sensor apparatus 100 includes one-dimensional (1D) nanostructures, such as those depicted in FIGS. 12-15. Such apparatus can include one or more of nanotubes, nanofibers, nanowires, and rods. A class of nanostructures includes nanoconductors. A nanostructure is said to be one dimensional, for example, if it much longer in one direction than in other directions perpendicular to the long direction, for example having a diameter on the order of a nanometer ($10^{-1}$ meters) and a length larger than 10 nm, larger than 50 nm, larger than 80 nm, larger than 90 nm or larger than 100 nm. Nanotubes include carbon nanotubes, for example. A nanowire is a nanostructure, with the diameter of the order of a nanometer ($10^{-1}$ meters). A nanostructure can be defined as the ratio of the length to width being greater than 1000. Many different types of nanowires exist, including superconducting (e.g., YBCO), metallic (e.g., Ni, Pt, Au), semiconducting (e.g., Si, InP, GaN, etc.), and insulating (e.g., $SiO_2$, $TiO_2$). As disclosed herein, a 1D nanostructure is densified and aligned to produce an effective conductor, which may be configured as a thin film.

Cost-effective technologies disclosed herein provide a process to highly density and align 1D nanostructures, such as CNTs, to improve its conductivity using shrink technology. In some embodiments, this is done by depositing a thin film of CNTs on the surface of a shape memory polymer, such as polyolefin. Preferably the polymer is a chemically resistant shape memory polymer. The process includes uniaxially, biaxially, or multiaxially shrinking the polymer by subjecting it to heat. Increasing the density and alignment of CNTs improves the conductivity of the assembly for strain gauge sensors and other applications that use CNTs. Other applications include batteries and chemical sensors.

We demonstrate that biaxial or multiaxially shrinkage of a CNT thin film produces wrinkled structures. As noted above, shrinking of metal films can produce wrinkling in the film. More generally, this wrinkling occurs if stiffness mismatch is provided between a substrate layer and a layer to be wrinkled or crumpled. We have found that a CNT thin film also produces wrinkling. It is believed that the total amount of van der Waals force between each individual CNTs is strong enough to create a stiff thin layer consequently wrinkling after biaxial or multiaxial shrinkage. This wrinkling phenomenon can be produced on shape memory polymers that shrink. We have also shown that the CNT thin film can be transferred onto a soft silicone substrate after removal of the shape memory polymer.

In some embodiments, the thin film of CNTs is shrunk by heating to a temperature of about 50° C., about 60° C., about 70° C., about 80° C., about 90° C., about 100° C., about 110° C., about 120° C., about 130° C., about 140° C., about 150° C., about 160° C., about 170° C., about 180° C. about 190° C., about 200° C., about 210° C., about 220° C., about 230° C., about 240° C., or about 250° C. or a range bounded by any two of the preceding numerical values.

A polyolefin is any of a class of polymers produced from a simple olefin (also called an alkene with the general formula $C_nH_{2n}$) as a monomer. For example, polyethylene is the polyolefin produced by polymerizing the olefin ethylene. An equivalent term is polyalkene.

In some embodiments, the CNTs are dispersed in a solution of an organic solvent, such as chloroform, prior to deposition on a shape memory polymer. Other non-limiting examples of organic solvents include benzene, toluene and phenyl ethyl alcohol or other solvents (Li et al. 2012 "Dispersion of Carbon Nanotubes in Organic Solvents Initiated by Hydrogen Bonding interactions" AlChE Journal 58: 2997-3002; Dumonteil et al. 2006 "Dispersion of carbon nanotubes using organic solvents" J Nanosci Nanotechnol 6(5): 1315-1318; and Austrian et al. 2000 "Organic Solvent Dispersions of Single-Walled Carbon Nanotubes: Toward Solutions of Pristine Nanotubes" J Phys Chem B 104: 8911-8915).

Densifying CNTs in a sensor application increases the sensitivity of the sensor, proportional to the degree to which a shape memory polymer shrinks. For example, a 95% reduction in area by shrinking on a polyolefin enables a much higher responsiveness. In some embodiments, a stretch senor or a strain gauge device, containing densified. CNTs, has a correspondingly lower electrical resistance upon densification of the CNTs. In some embodiments, the resistance of a film upon densification is reduced to about 100 kΩ. In some embodiments, the resistance of a film upon densification is reduced to about 10 kΩ, about 50 kΩ, about 100 kΩ, about 150 kΩ, about 200 kΩ, about 250 kΩ, about 300 kΩ, about 350 kΩ, about 400 kΩ, about 450 kΩ, about 500 kΩ, about 550 kΩ, about 600 kΩ, about 650 kΩ, about 700 kΩ, about 750 kΩ, about 800 kΩ, about 850 kΩ, about 900 kΩ, about 950 kΩ, about 1000 kΩ, about 1100 kΩ, about 1200 kΩ, about 1300 kΩ, about 1400 kΩ or about 1500 kΩ or a range bounded by any two of the preceding numerical values. A low resistance film allows the development of highly sensitive devices that were previously not feasible based on previously existing technologies.

In some embodiments, the density amplification of the CNTs relative to an initial density upon application of the CNTs to a shape memory polymer is an increase of about 100%, about 150%, about 200%, about 250%, about 300%, about 350%, about 400%, about 450%, about 500%, about 550%, about 600%, about 650%, about 700%, about 750%, about 800%, about 850%, about 900%, about 950%, about 1000%, about 1100%, about 1200%, about 1300%, about 1400% or about 1500% or a range bounded by any two of the preceding numerical values.

CNT density can be measured by a light transmittance test. In some embodiments, the CNT density results in light transmittance values of between about 30 to about 90%. In some embodiments the light transmittance is about 30%, about 35%, about 40%, about 45%, about 50%, about 55%, about 60%, about 65%, about 70%, about 75%, about 80%, about 85% or about 90% or a range bounded by any two of the preceding numerical values.

Examples Applications of Wrinkled CNT Structures

1. Flexible Devices

Wrinkled CNT thin films can be incorporated into flexible devices, such as in sensor apparatuses, including strain gauges. As noted above, the CNT thin films can form the sensing component of the sensor apparatus 100. An advantage of using wrinkled films in flexible devices is the ability to stretch out the wrinkles produced from shrinking. Depending on the shape memory polymer used, it is theoretically possible to stretch out to the original, pre-shrinkage dimensions.

Various applications benefit from strain gauges that can undergo large strains and still produce repeatable, predictable outputs. For example, it is desired that such a strain gauge or other sensor apparatuses can be mounted on a flexible substrate and connected to surfaces that are highly curved, mobile and/or repeatedly flexed during the duty cycle of the strain gauge or sensor apparatus. It would be useful for a sensor apparatus herein to be wearable to enable various health or physiological condition monitoring applications, such as for monitoring fetal or maternal health and more comprehensively progress of a pregnancy.

2. Piezoresistive and Capacitive Sensors with Wrinkled CAT Structures

Wrinkled CNT thin films can also be used in the fabrication of piezoresistive and capacitive sensors (Limpomi, D. J.; Vosgueritchian, M.; Tee, B. C-K.; Hellstrom, S. L.; Lee, J. A.; Fox, C. H.; Bao, Z. *Nature Nanotech.* 2011, 6, 788-792, incorporated herein by reference). As such CNT thin films can be used to provide a capacitive sensor for monitoring fetal or maternal health and more comprehensively progress of a pregnancy. Elastic conductors are advantageous components for use in electronic and optoelectronic devices that facilitate human interaction and biofeedback, such as interactive electronics, implantable medical devices and robotic systems with human-like sensing capabilities. The availability of conducting thin films with these properties provides a basis for the development of skin-like sensors that stretch reversibly, sense pressure, bend into hairpin turns, integrate with collapsible, stretchable and mechanically robust displays and solar cells, and also wrap around non-planar and biological surfaces such as skin and organs.

B. STRETCHABLE INTERCONNECTS

Figure 20:
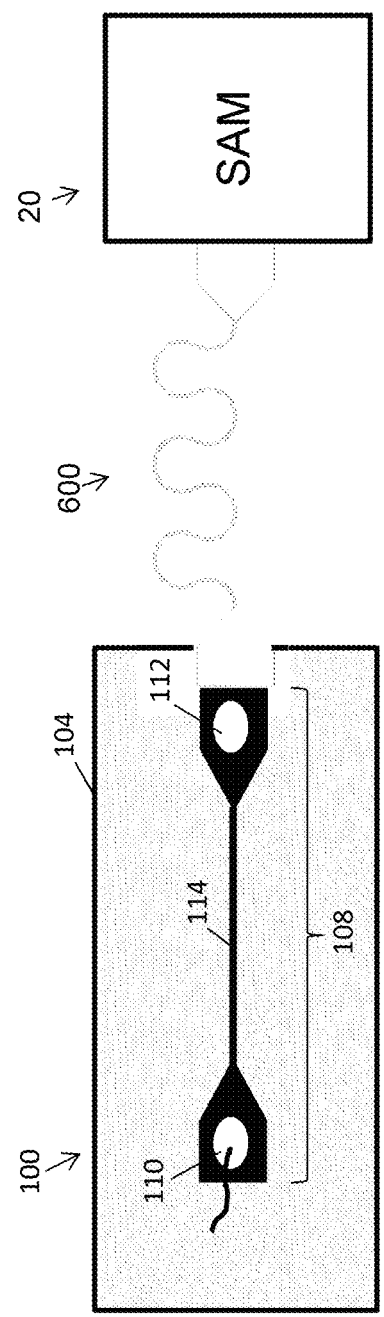
FIG. 20 depicts an assembly including a stretchable conductive interconnect, a sensor apparatus, and a sensor attachment module.

Stretchable conductive interconnects have applications in wearable electronic devices, clothing and integrated textiles. Disclosed herein are materials and design methods for fabricating stretchable conductive interconnects, as depicted in FIGS. 16 and 17. They are applicable in electronic apparatuses where there is a desire for high electronic performance that is unaffected by mechanical strain. Examples of applications include wearable electronics, smart or integrated textiles, and/or increasing the reliability of electronics in harsh environments. Referring to FIG. 20, such interconnects can be useful for connecting the sensor device 100 to the sensor attachment module (20) so that the signal from the device 100 will be reliably transmitted to the pregnancy monitoring system over the period of use, which can be for one or a few hours or for a day or more. The stretchable interconnect components can be useful for extending the life-cycle of the sensor device 100.

The rapidly growing field of wearable electronics integrates electronics into daily life. Importantly, the promise of electronics integrated with the human body opens up the possibility for continuous, remote health monitoring. This will help to enable more efficient preventative healthcare, personalized treatment and rehabilitation therapies, and low healthcare costs. However, current devices remain crude, consisting of pre-existing electronic components mounted onto the human body, often with poor sensor performance and diminished patient dignity.

Biological systems, such as the human body, are typically harsh environments for electronics. Electronics, most being planar and rigid must perform in environments that are soft, stretchable, curvilinear, and moist. Even integrated systems that utilize small, thin components that can be packaged into a wearable form factor, must connect every component with standard wire or printed metal lines as conductive interconnects. Electrical wires must be made long in order to deal with high strain environments to avoid breaking. They still present significant hazards in terms of tangling and catching on the user or other objects. Printed metal lines, although unobtrusive, are brittle and break under the high strains present on the human body.

There are two major categories of stretchable, conductive interconnects: conductive polymers (Noh, 2014 *RSC* 4: 1857-1863) and microfluidics with conductive liquids (Cheng, S. et al. 2012 *Lab Chip* 12: 2782-2791). Conductive polymers are more flexible than metal interconnects. However, they typically exhibit strong piezoresistive characteristics and have poor conductivity compared to metals. Conductive microfluidic interconnects can be molded into elastic materials. The conductive fluid maintains consistent conductivity under high strain as the fluid maintains the geometry of the microfluidic channel. However, this type of interconnect is hard to fabricate due to the complexities of injecting conductive fluid into microfluidic channels. Proper sealing of the channel ends is crucial and there exists an additional solid interface required to electrically connect the conductive fluid with the solid electrical component.

The stretchable conductive interconnects disclosed herein enable integrated systems as a modular design approach to wearable sensors. The conductive material (see FIG. 17, CM) is fabricated and transferred into stretchable elastomeric materials (see FIG. 17, EM) that can be mounted to, conformed with, and stretched with human skin. In some embodiments, the conductive material is encapsulated in an insulating elastomeric material, also making the stretchable interconnects waterproof. All other electronic components can be packaged separately and interface with each other using these stretchable interconnects to complete a wearable system.

Figure 19:
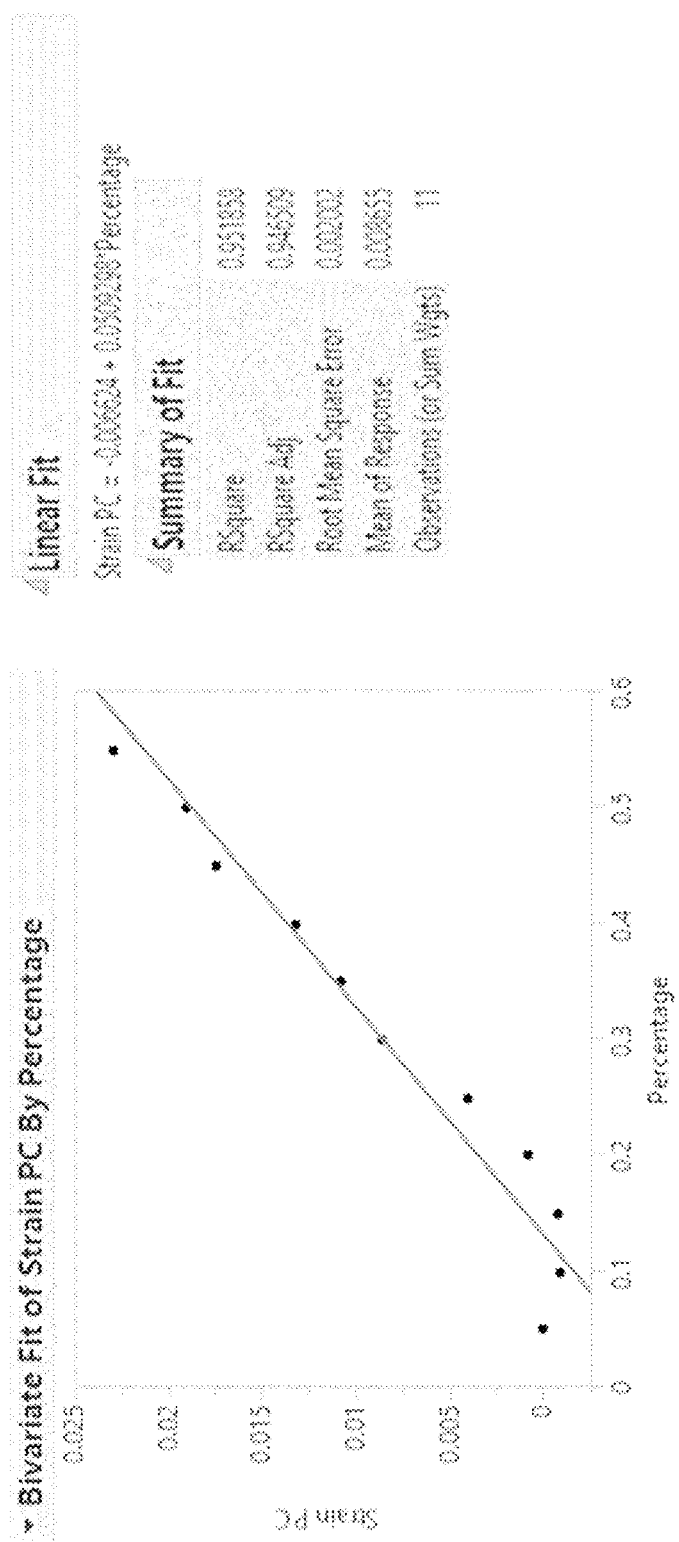
FIG. 19 shows gauge factor of a stretchable interconnect.

The use of a wrinkled metal film, fabricated using shape memory polymers, improves on the mechanical properties of stretchable interconnects (Pegan J. et al. 2013 Lab Chip 13: 4205-4209, incorporated herein by reference). Combining a wrinkled metal film with strain relieving geometrical designs and soft elastomeric substrates allows for a stretchable, conductive interconnect that maintains high conductivity under mechanical strain. In some embodiments, a serpentine pattern is used. Arc angles (601 in FIG. 16) of a serpentine pattern may be varied, e.g., from 60°, 80°, 90°, 100°, 110°, 120°, 130°, 140°, 150°, 160°, 170°, 180°, 190°, 200°, 210°, 220°, 230°, 240°, 250°, 260°, 270°, 280°, 290°, 300°, 310°, 320°, 330°, 340° and 350°. The radius (602 in FIG. 16) of loops in a serpentine pattern may also vary, e.g., from 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm and 15 mm. The thickness of an interconnect (603 in FIG. 16) may vary from 0.1 mm, 0.2 mm, 0.3 mm, 0.4 mm, 0.5 mm, 0.6 mm, 0.7 mm, 0.8 mm, 0.9 mm, 1 mm, 1.5 mm and 2 mm. The length of an interconnect (604 in FIG. 16) will vary, depending on the particular application. For example, the length may be 10 mm, 15 mm, 20 mm, 25 mm, 30 mm, 35 mm, 40 mm, 45 mm, 50 mm, 55 mm, 60 mm 65 mm 70 mm, 75 mm, 80 mm, 85 mm, 90 mm, 95 mm, 100 mm, 110 mm, 120 mm, 130 mm, 140 mm, 150 mm, 160 mm, 170 mm, 180 mm, 190 mm and 200 mm. In one embodiment, a serpentine pattern may have arc angles of 120°, a 5 mm radius, a 0.5 mm thickness, and a 54.55 mm length. The length of the conductive interconnect can be extended as needed. In cases where an interconnect is fabricated as a wrinkled conductive structure, methods disclosed herein can be used to shrink the conductive structure. For example, a polymeric sheet (e.g., polystyrene) can be shrunk (e.g., by approximately 300%) using a heat source, such as a conventional toaster oven to induce wrinkling in the metal film. Dimensions of the pre-shrunk device are also shrunk by approximately 300%. The geometric parameters of the interconnect, such as arc angles are correspondingly reduced in size. The wrinkled metal film is then transferred. The strain relieving design reduces the strain on the conductive metal film as much as 50%, 100%, 150%, 200%, 250%, 300%, 350% or 400%. Additionally, because the metal film is compressed by 300% by a wrinkling process, it can unwrinkle or unfold as much as 300% before the metal film is subject to elastic or plastic strain and subsequently broken. Referring to FIG. 19, at up to 55% strain, the gauge factor is approximately 0.05. The gauge factor is relative change in resistance (R) divided by amount of strain (ε), which is a good indicator of how reliable the stretchable interconnect is.

Advantages of stretchable conductive interconnects include mechanical and electrical robustness under high strain. They can withstand strains up to 400% and maintain stable electrical conductivity (>3.5% change) at 70% strain. The fabrication process is low-cost and relatively quick compared to other stretchable interconnects, which require more complicated fabrication processes such as photolithography. Many stretchable interconnects are also physically limited by the substrate on which the device is fabricated. Some embodiments disclosed herein use a soft silicone elastomer that is able to withstand strains up to 900%. The stretchable conductive interconnects can also be easily incorporated into conformal electronics that require flexibility such as wearable electronics.

C. PREGNANCY MONITORING SYSTEM FUNCTIONAL FLOW

Figure 21:
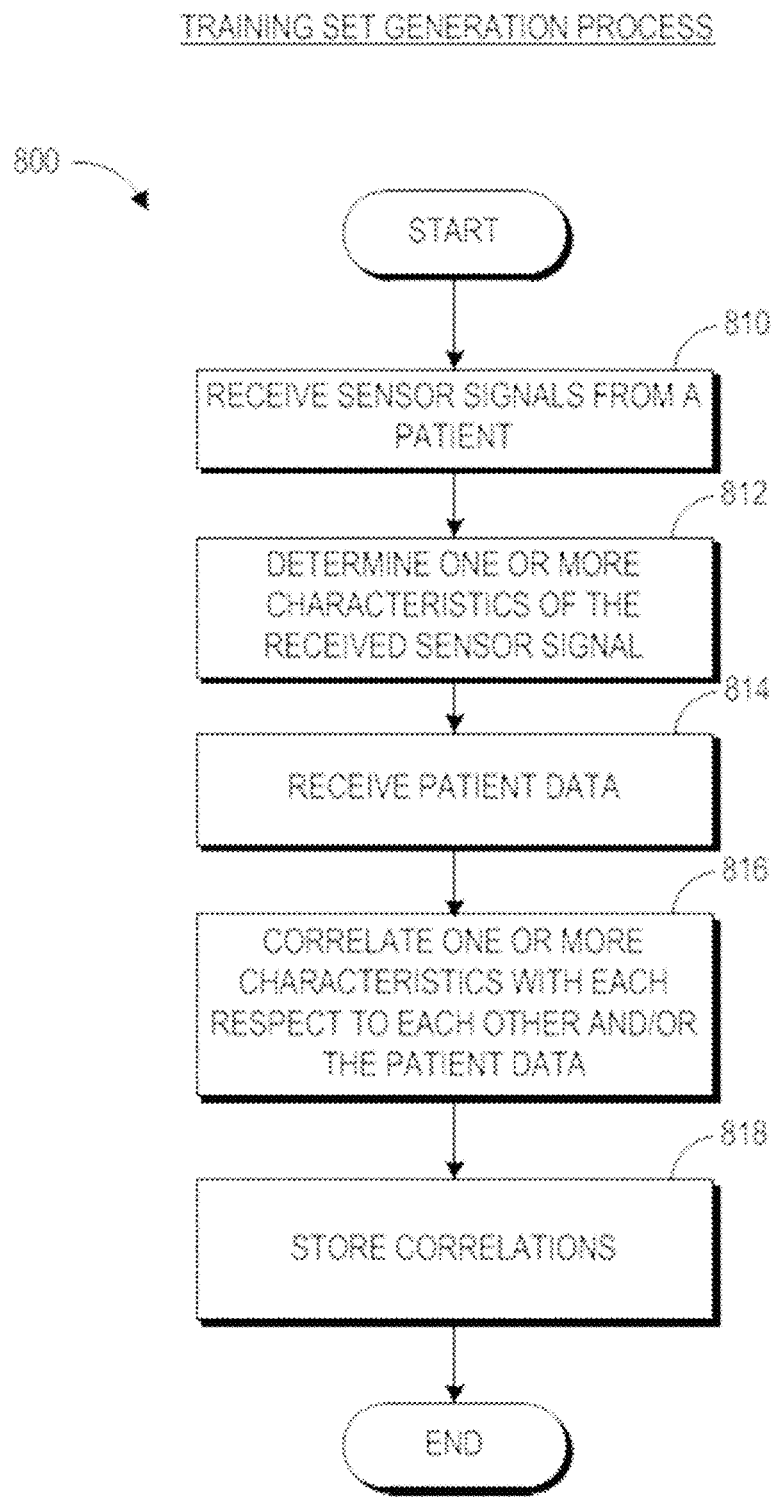
FIG. 21 shows a training set generation process.

FIG. 21 illustrates an embodiment of a method 800 for determining correlations between signal data from the sensor 100 and pregnancy characteristics. The method 800 can be implemented by any of the systems described herein, in some embodiments, the method 800 is implemented by the PMS 40 described above with respect to FIGS. 1 and 3.

The process 800 begins at block 810 with receiving sensor signals from a sensor 100 attached to a patient 85. For the purposes of generating a training set, the sensor data can be collected over a period of time and for multiple patients. The period of time can include hours, days, or weeks. In an embodiment, the received sensor data from multiple patients over a period of time is stored in a data repository 76.

At block 812, the calculator module 54 can determine one or more properties of the received sensor signal. For example, the calculator module 54 can determine electrical signatures, including but not limited to the shape, frequency, magnitude, displacement, or width from the received sensor signals.

At block 814, the remote system 70 can receive patient data corresponding to the patients associated with the received signals. Patient data can include patient parameters, such as age of the patient, number of weeks pregnant, weight, and the like. Patient data can also include observed data corresponding to the received signal. For example, the received signal can be tagged with events. If a patient feels a kick, the corresponding sensor data may be tagged with the kick event. Additional patient data can include data corresponding to a mother's activity, for example, having a meal. Tagging sensor data with the patient data such that the patient events are approximately synchronized in time with the sensor data can be advantageous in some embodiments for determining correlations. Dynamic patient parameter such as weight or number of weeks pregnant may also be tagged with the corresponding sensor data.

The calculator module 54 can use the patient data such as tagged data or patient parameters to determine relationships or correlations with signal characteristics. In one embodiment, the calculator module 54 uses machine learning algorithms to determine correlation between one or more characteristics of the sensor data. Machine learning can evaluate multiple parameters simultaneously without a priori knowledge; therefore, it can discover unexpected relationships to potentially yield better detection. Furthermore, machine learning can provide a singular quantitative index that can summarize the impact of multiple parameters. Machine learning algorithms can be used, for example, to determine uterine wall contractions based on monitoring of fetal movement. Machine learning algorithms can include supervised, such as Support Vector Machine (SVM) or unsupervised, such as k-nearest neighbors algorithms. The calculator module 54 can also use decision tree and regressions-based models to determine correlations and predict outcomes.

In one embodiment, the calculator module 54 uses a Support Vector Machine (SVM) algorithm. The calculator module 54 can use the training data to create an optimal model with generalizability. In an embodiment, the calculator module 54 can classify the data points into two groups (e.g. fetal movement v. uterine wall contractions) by creating a decision boundary that separates the two groups. The model can be evaluated by classifying unseen or withheld data. To ensure that over-fitting does not occur and that the classification model has good generalizability to new data, cross validation can be performed by the calculator module 54. Machine learning algorithms can also identify other classifications from the received sensor data.

At block 818, the correlations or models generated by the calculator module 54 can be stored in a data repository 76. The stored correlations can be used for monitoring a pregnant mother and also determining current and future indicators.

Figure 22:
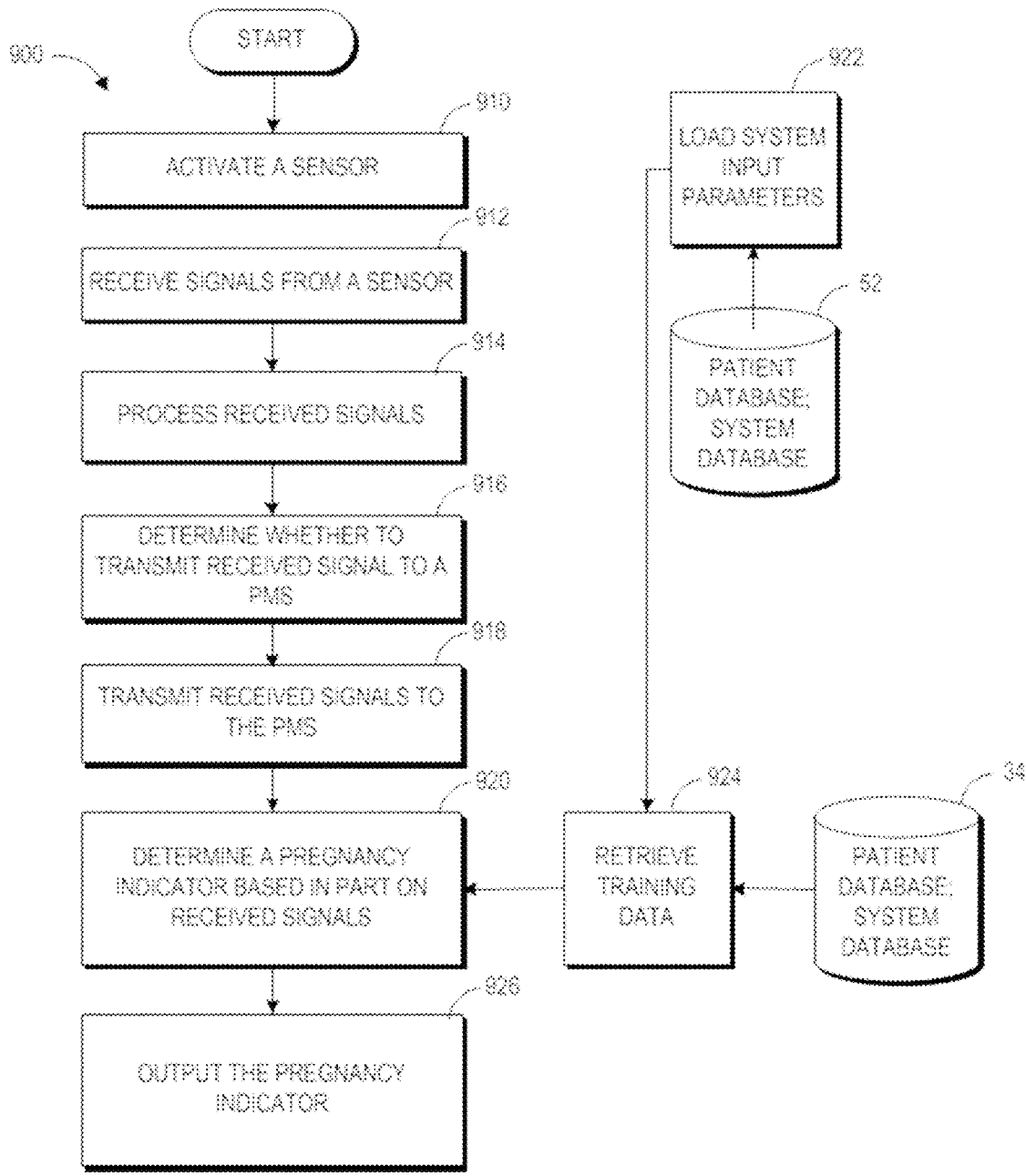
FIG. 22 shows a frequency monitoring system functional flow.

FIG. 22 illustrates an embodiment of a process 900 for monitoring an expectant mother using the sensor 100. The process 900 can be implemented by any of the systems described herein. In some embodiments, the process 900 is implemented by the PMS 10 described above with respect to FIGS. 1 and 3.

The process 900 can begin at block 910 when the processor 24 sends a signal to the measuring circuit 32 to measure a voltage output from a sensor 100 affixed to an expecting mother. The voltage measurement can correspond to a change in resistance or strain of the sensor 100. The processor 24 can receive the measurement signals from the sensor 100 and store it in the memory 26 at block 912. The memory 26 may include a buffer for storing signals, which may be cleared by the processor 24 when the signals are transmitted from the SAM 20.

In some embodiments, the processor 24 can process received signals at block 914 before transmission. Processing can involve extracting a characteristic, such as a frequency, amplitude, or any other signature of the received signals.

At block 916, the processor 24 can determine whether to transmit received signals stored in the memory 26. The determination can be based on the processing of the received signals. For example, the processor 24 can compare the frequency or amplitude extracted from the received signals to a predetermined threshold. As an example, the processor 24 can transmit the received signals when the frequency of the kicks exceeds 10 kicks per 2 hours. In some embodiments, the processor 24 transmits the received signals in response to a request from the user system 10. Further, the processor 24 may also be programmed to transmit the received signals after a predetermined time period, for example, every 30 minutes or 1 hour or 2 hours. The predetermined time period does not need to be a constant and can be a function of the patient data.

At block 918, the radio circuit 22 can transmit the received signals to a user system 10. In an embodiment, signals are transmitted using the Bluetooth protocol. The PMS 40 can perform additional processing on the received signals to determine a pregnancy indicator at block 920. The PMS 40 includes the signal collector module 52 to access the transmitted signals from SAM 20. In some embodiments, the PMS 40 transmits the received signals over a network 74 to the remote system 70 for determination of the pregnancy indicator or to process at least some aspects of the received signals. The remote system 70 may have access to higher processing and data resources as compared to the PMS 40 and SAM 20 for analyzing received signals. Accordingly, it may advantageous in some embodiments to have the processor 72 implement aspects of the calculator module 54, such as the machine learning algorithm, that requires more processor intensive resources.

In an embodiment, the calculator module 54 applies the system parameters, such as models and correlations (as discussed above with respect to FIG. 21 to the received signal data to determine a pregnancy indicator. For example, the calculator module 54 can analyze the received signal data and determine whether it belongs in the class corresponding to the fetal movement or uterine wall contractions. Other indicators of pregnancy can include number of kicks over a period of time. For instance, if the frequency of the kicks decreases, it may indicate a health issue. The calculator module 54 may generate an alert at block 926. The I/O module 56 can notify the mother by displaying the alert or outputting a sound or a signal (e.g. vibration) at the user system 10. In addition to any alerts, the calculator module 54 may also generate results of the analysis of the received signals. The I/O module 56 can also output a trend chart based on the results.

In some embodiments, the calculator module 54 can also use patient-specific parameters stored in patient data repository 58 or 76 to determine the pregnancy indicator. A mother can also input parameters, such as her weight or whether she had a meal, using the I/O module 56. The calculator module 54 can use all the available data to determine one or more pregnancy indicators.

D. EXAMPLES

Example 1

Processing Guide for Transferring a Structured Metal Thin Film from a Shape-Memory Carrier onto a Silicon Elastomer This protocol is meant to serve as a processing guide for transferring wrinkled metal thin films from a substrate (e.g., Grafix Arts polystyrene shrink film) onto an elastomer (e.g., ECOFLEX30™ silicon elastomer). Specific parameters are given for platinum strain gauges and gold interconnects. Adjustments may be made for specific process applications.

Grafix Frisket Film is mounted to rigid PMMA support. A mask design is laser cut using Grafix Frisket Film using laser settings of 75% power and 100% speed. For convenience, scotch tape is placed across trace width before removing the mask from the support (in order to not distort trace width).

b. Polystyrene (PS) SMP (Grafix Arts)

Grafix PS sheets are laser cut with laser settings of 78% power, 100% speed and placed concave up (using weights to flatten edges) and then ligned length to length (orient such that long side is aligned with axis being stretched). The cut PS are washed with 70% EtOH and air dried. Alignment of the mask is made by peeling off the mask and setting on desk with adhesive side up. The PS sheet is taken up with concave side down and bend both edges so that the center will adhere first before smoothing it down along the sides c. Deposition Sputter deposition is used, setting Argon gas pressure to 4 psi using a vacuum pump. Check target and set target metal and run test: 2-5 nm terminal thickness. For strain gauges, use Platinum (10 nm). For interconnects, use Gold (15 nm).

2. Miniaturization

Bake using a toaster oven preheated to 160° C., shrinking samples 2-4 at a time. Let cool to room temperature before removing samples from baking tray 3. Anneal Preheat vacuum oven to 200° C. for ½-1 hour and bake for 15 min at 200° C. Place samples on copper plate and cool at room temp for 2 min. Repeat for 3× total. If curing ECOFLEX™ in same day, immediately set oven to 85° C. and open oven door)

4. Silane Treatment (Application of Adhesion Layer)

Prepare 5 mM of Mercaptorpopyl trimethoxy-silane in EtOH (e.g., 38 µm silane in 40 mL EtOH). Place samples in petri dish and pour silane solution over it (can do up to 6 samples at once per dish). Parafilm shut and leave for 1 hr at room temp. Rinse samples individually with EtOH wash bottle and an dry before preceding to transfer.

5. Transfer

For EF30 (ECOFLEX™) elastomer, mix components A:B at a 1:1 ratio. Degas: 5 min (pot Life: 45 min, cure time (rm temp): 4 hours). For spin coating, use program 4: Step 1: Ramp 300 rpm for 5 sec; Step 2:150 rpm 30 sec, acceleration is at 1200 rpm per min. For vacuuming and curing, vacuum for 20 min and cure in vacuum oven for 2 hours at 85° C. (can be left in overnight). For Etch ECOFLEX™ (EF), laser cut EF and place onto paper (use weights to flatten paper; Materials Database: Copier Paper). For laser cutting, use laser settings of 99.4% power, 100% speed, Use outline in paper to align sample. Scale as necessary as shrink process may cause variations in aspect ratio. For laser cut samples, use EF30,_1 mm, with laser settings of 100% power, 31% speed. For liftoff, use the following solvent baths: Acetone: 30 min at 55° C.; toluene: 10 min at 70° C. (gently agitate on hot plate in the last min or two). To dry, hang dry by corners using binder clips overnight.

Example 2

Densification and Alignment of CNTs Using Polyolefin

This was accomplished by first dispersing CNTs (0.05% wt/v) in a solution of chloroform. CNTs were sonicated for 30 minutes in an ice bath and centrifuged at 10,000 rpm for one hour. This process is also possible in aqueous solution. For example, CNTs can be dispersed into an aqueous solvent when a surfactant, such as sodium dodecyl sulfate (SDS), is present (Yu, J.; Grossiord, N.; Konin, C. E.; Loos, J. *Carbon*. 2007, 45(3), 618-623). The shape memory polymer was then heated to approximately 60° C. after which drop casting deposition was used to create a thin layer of CNTs. Drop casting is done by pipetting the CNT disperse solution on top of the heated shape memory polymer. The shape memory polymer was then left to dry in a closed container for two hours. In the case of using aqueous CNTs, after the shape memory polymer is dried, it is further washed with an aqueous solvent to remove any surfactants present on the shape memory polymer. The shape memory polymer is then left to dry in a closed container for two hours. After drying, the shape memory polymer was then clamped to a glass slide on two ends for uniaxial shrinking. The shape memory polymer was then shrunk in a conventional toaster oven at 150° C., which densified and aligned the CNTs on the surface of the shape memory polymer.

This process is extremely fast and efficient compared to other time consuming processes such as the Langmuir-Blodgett method. The process is very reproducible and does not require much dexterity. The density amplification of the CNTs is up to 770% due to the shrinking nature of polyolefin, which is more than two folds higher than previous shrinking technology. The process can also be done using almost any solvent suitable for obtaining a stable CNT dispersion.

Example 3

Biaxial or Multi-axial Shrinkage of a CNT Thin Film to Produce a Wrinkled Structure One embodiment is a process to densify a CNT thin film to produce wrinkled structure using polyolefin, a chemically resistant shape memory polymer. This was accomplished by first dispersing CNTs (0.05% wt/v) in a solution of chloroform. CNTs were sonicated for 30 minutes in an ice bath and centrifuged at 10,000 rpm for one hour. This process is also possible in aqueous solution. For example, CNTs can be dispersed into an aqueous solvent when a surfactant, such as sodium dodecyl sulfate (SDS), is present (Yu, J.; Grossiord, N.; Konin, C. E.; Loos, J. *Carbon*. 2007, 45(3), 618-623). The shape memory polymer was then heated to approximately 60° C. after which drop casting deposition was used to create a thin layer of CNTs. Drop casting is done by pipetting the CNT disperse solution on top of the heated shape memory polymer. The shape memory polymer was then left to dry in a closed container for two hours. In the case of using aqueous CNTs, after the shape memory polymer is dried, it is further washed with an aqueous solvent to remove any surfactants present on the shape memory polymer. The shape memory polymer is then left to dry in a closed container for two hours. After drying, the shape memory polymer was permitted to undergo biaxial shrinking. The shape memory polymer was then shrunk in a conventional toaster oven at 150° C., resulting in a densified SiNW network on the surface of the shape memory polymer.

This process is extremely fast and efficient compared to other time consuming processes such as the Langmuir-Blodgett method. The process is very reproducible and does not require much dexterity. The density amplification of the CNTs is up to 770% due to the shrinking nature of polyolefin, which is more than two fold higher than previous shrinking technology. The process can also be done using almost any solvent suitable for obtaining a stable CNT dispersion.

Example 4

Deposition of a Confluent Film of Carbon Nanotubes onto the Surface of a Polyolefin In another process, a confluent film of carbon nanotubes is deposited onto the surface of a shape memory polymer, such as a polyolefin. In one embodiment, an airbrush is used to facilitate deposition of a confluent film of CNTs and greatly speed up the process.

Example 5

Biaxial or Multi-axial Shrinking of a Silicon Nanowire (SiNW) Thin Film

SiNWs were synthesized by Si wafer using aqueous Ag-assisted electroless etching. A P-type, (1,0,0), 1-100 Ω/cm Si wafer was used to synthesize SiNWs in an aqueous solution of 0.02M AgNO3 and 5M HF acid. The lengths of the SiNWs can be controlled by the etching time. To remove the SiNWs from the Si wafer, the Si substrate was sonicated in isopropyl alcohol (IPA) for 30 seconds. The shape memory polymer was then heated to approximately 60° C. after which drop casting deposition was used to create a thin layer of SiNWs. Drop casting is done by pipetting the SiNW solution on top of the heated shape memory polymer. The shape memory polymer was then left to dry in a closed container for two hours. After drying, the shape memory polymer was permitted to undergo biaxial shrinking. The shape memory polymer was then shrunk in a conventional toaster oven at 150° C., resulting in a dense SiNW network on the surface of the shape memory polymer.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A wearable strain gauge, comprising:
   a flexible substrate adapted to conformally coupled with a user's skin,
   a conductor deposited on the flexible substrate, wherein the conductor comprises micron-scale invaginations, wherein adjacent micron-scale invaginations make physical contacts with each other between non-contiguous positions in the adjacent micron-scaled invaginations, wherein the physical contacts between non-contiguous positions in the adjacent micron-scaled invaginations are configured to reduce an effective resistivity of the conductor.

2. The wearable strain gauge of claim 1, wherein the micron-scale invaginations comprise a heterogeneous topographical portion.

3. The wearable strain gauge of claim 1, wherein the flexible substrate is configured to be mounted to an abdomen of the user.

4. A wearable strain gauge comprising a film of a highly dense and aligned one-dimensional structures.

5. The wearable strain gauge of claim 4, wherein the highly dense and aligned one-dimensional structures are selected from the group consisting of a nanotube, a nanofiber, a nanowire and a rod.

6. The wearable strain gauge of claim 5, wherein the nanotube is a carbon nanotube (CNT).

7. The wearable strain gauge of claim 5, wherein the nanowire is a silicon nanowire.

8. The wearable strain gauge according to claim 4, wherein an electrical resistance of the highly dense and aligned one-dimensional structures is about 300 kΩ.

9. The wearable strain gauge according to claim 1, wherein the conductor further comprises nanometer-scaled invaginations.

10. A method of sensing a health condition of a pregnant mother, comprising:
    coupling a wearable strain gauge according to claim 1 to an abdominal surface of the pregnant mother overlying the uterus;
    directing current through the wearable strain gauge during flexing of the abdominal surface; and
    measuring a characteristic of the wearable strain gauge based on a strain to generate an output for a user indicative of the health of a fetus and/or a status of pregnancy.

11. The method of claim 10, wherein the characteristic of the wearable strain gauge is a change in the resistance of the conductor thereof.

12. The method of claim 10, wherein movement of the surface is in response to breathing of the pregnant mother and the output indicates respiration of the pregnant mother.

13. The method of claim 10, wherein movement of the abdominal surface is in response to motion of an underlying structure.

14. The method of claim 10, wherein the wearable strain gauge is flexible to be secured to and conform to the abdominal surface of the pregnant mother.

15. The method of claim 10, wherein movement of the abdominal surface is in response to movement of the fetus in utero.

16. A system for monitoring health of a fetus in utero, comprising:
a wearable strain gauge according to claim 1 configured to output a signal responsive to an electrical input;
a computing system comprising one or more hardware processors, said computing system programmed to implement:
a signal processing module configured to:
access the signal from the wearable strain gauge; and
generate an output indicative of health of the fetus in utero based in part on the signal and previously stored correlations between signal data from wearable strain gauge and observations of the system or of a mother of the fetus; and
a user interface module configured to display the output indicative of health of the fetus in utero.

17. The system of claim 16, wherein the computing system is further programmed to implement a machine learning module configured to determine said correlations between signal data from wearable strain gauge and observations of the system or of the mother of the fetus using a machine learning algorithm.

18. The system of claim 17, wherein the machine learning module comprises a support vector machine.

19. The system of claim 17, wherein the machine learning module comprises unsupervised monitoring.

20. The system of claim 19, wherein the machine learning module comprises k-nearest neighbors.

21. The system of claim 17, wherein the machine learning module is adapted to discern uterine wall contractions from movement of a baby.

22. The system of claim 17, wherein the machine learning module is adapted to discern smooth muscle movement or diaphragm movement from the mother of the fetus.

23. The system of claim 22, wherein said smooth muscle movement is contractions.

24. The system of claim 22, wherein said diaphragm movement is respiration.

25. The system of claim 16, further comprising a physical display configured to communicate health status signals to a user.

26. The system of claim 25, wherein the health status signals are generated and displayed in real time.

* * * * *